(12) United States Patent
Plaimauer et al.

(10) Patent No.: US 9,127,264 B2
(45) Date of Patent: Sep. 8, 2015

(54) SUBSTANTIALLY ANIMAL PROTEIN-FREE RECOMBINANT FURIN AND METHODS FOR PRODUCING THE SAME

(75) Inventors: Barbara Plaimauer, Vienna (AT); Simone Von Fircks, Vienna (AT); Leopold Grillberger, Vienna (AT); Meinhard Hasslacher, Vienna (AT); Roland Geyer, Vienna (AT); Artur Mitterer, Orth/Donau (AT); Manfred Reiter, Vienna (AT)

(73) Assignees: BAXALTA INCORPORATED, Bannockburn, IL (US); BAXALTA GMBH, Glattpark (Opfikon) (CH)

( * ) Notice: Subject to any disclaimer, the term of this patent is extended or adjusted under 35 U.S.C. 154(b) by 1058 days.

(21) Appl. No.: 12/960,093

(22) Filed: Dec. 3, 2010

(65) Prior Publication Data

US 2011/0076719 A1 Mar. 31, 2011

Related U.S. Application Data

(63) Continuation of application No. 12/339,597, filed on Dec. 19, 2008, now abandoned.

(60) Provisional application No. 61/018,152, filed on Dec. 31, 2007.

(51) Int. Cl.
| | |
|---|---|
| *C12P 21/06* | (2006.01) |
| *C12N 9/50* | (2006.01) |
| *C07H 21/04* | (2006.01) |
| *C07K 1/00* | (2006.01) |
| *C12N 9/64* | (2006.01) |

(52) U.S. Cl.
CPC .................. *C12N 9/6454* (2013.01)

(58) Field of Classification Search
CPC ................................. C12N 9/6454
USPC .............. 435/68.1, 69.1, 219; 536/23.2, 23.1; 530/350
See application file for complete search history.

(56) References Cited

U.S. PATENT DOCUMENTS

| | | | |
|---|---|---|---|
| 6,210,929 B1 | 4/2001 | Schlokat et al. | |
| 6,596,526 B1 | 7/2003 | Plaimauer et al. | |
| 7,067,059 B2 * | 6/2006 | Maloisel et al. | 210/635 |
| 7,955,833 B2 * | 6/2011 | Reiter et al. | 435/235.1 |
| 2007/0167613 A1 * | 7/2007 | Johansson et al. | 530/389.1 |
| 2007/0212770 A1 | 9/2007 | Grillberger et al. | |

FOREIGN PATENT DOCUMENTS

| | | |
|---|---|---|
| EP | 0775750 A | 5/1997 |
| WO | WO-91/06314 | 5/1991 |
| WO | WO-92/09698 | 6/1992 |
| WO | WO-98/15614 | 4/1998 |
| WO | WO-00/49047 | 8/2000 |
| WO | WO-01/94383 | 12/2001 |
| WO | WO-03/042233 A2 | 5/2003 |
| WO | WO-2008/141824 A2 | 11/2008 |

OTHER PUBLICATIONS

Cameron et al., "Polyarginines are potent furin inhibitors," *J. Biol. Chem.* 275:36741-9 (2000).
Ayoubi et al., Production of recombinant proteins in Chinese hamster ovary cells overexpressing the subtilisin-like proprotein converting enzyme furin, *Mol. Biol. Reports* 23:87-95 (1996).
Barr et al., cDNA and gene structure for a human subtilisin-like protease with cleavage specificity for paired basic amino acid residues, *DNA Cell Biol.* 10:319-28 (1991).
Barr, Mammalian subtilisins: The long-sought dibasic processing endoproteases, *Cell* 66:1-3 (1991).
Bresnahan et al., Human fur gene encodes a yeast KEX2-like endoprotease that cleaves pro-beta-NGF in vivo, *J. Cell Biol.* 111:2851-9 (1990).
Bristol et al., Profactor IX: the propeptide inhibits binding to membrane surfaces and activation by factor XIa, *Biochemistry* 33:14136-43 (1994).
Broun et al., Catalytic plasticity of fatty acid modification enzymes underlying chemical divercity of plant lipids, *Science* 282:1315-7 (1998).
Chiron et al. Furin-mediated cleavage of pseudomonas exotoxin-derived chimeric toxins, *J. Biol. Chem.* 272:31707-11 (1997).
Chun et al., Usability of size-excluded fractions of soy protein hydrolysates for growth and viability of Chinese hamster ovary cells, *Bioresource Technol.* 98:1000-5 (2007).
Creemers et al., Modulation of furin-mediated proprotein processing activity by site-directed mutagenesis, *J. Biol. Chem.* 268:21826-34 (1993).
Database GenBank. National Center for Biotechnology Information, U.S. National Library of Medicine, (Bethesda, MD, US) Accession No. EAX02111, Furin (paired basic amino acid cleaving enzyme), isoform CRA_a [Homo sapiens], Dec. 18, 2006.
Decroly et al., The convertases furin and PC1 can both cleave the human immunodeficiency virus (HIV)-1 envelope glycoprotein gp160 into gp120 (HIV-1 SU) and gp41 (HIV-I TM), *J. Biol. Chem.* 269:12240-7 (1994).
Devos et la., Practical limits of function prediction. Proteins: Structure, Function, and Genetics. 41: 98-107 (2000).
Hatsuzawa et al., Molecular and enzymatic properties of furin, a Kex2-like endoprotease involved in precursor cleavage at Arg-X-Lys/Arg-Arg sites, *J. Biochem.* 111:296-301 (1992).
Hatsuzawa et al., Purification and characterization of furin, a Kex2-like processing endoprotease, produced in Chinese hamster ovary cells, *J. Biol. Chem.* 267:16094-9 (1992).
Hatsuzawa et al., Structure and expression of mouse furin, a yeast Kex2-related protease. Lack of processing of coexpressed prorenin in GH4C1 cells, *J. Biol. Chem.* 265:22075-8 (1990).
Hosaka et al., Arg-X-Lys/Arg-Arg motif as a signal for precursor cleavage catalyzed by furin within the constitutive secretory pathway, *J. Biol. Chem.* 266:12127-30 (1991).
Keen et al., Development of a serum-free culture medium for the large scale production of recombinant protein from a Chinese hamster ovary cell line, *Cytotechonol.* 17:153-63 (1995).
Kiefer et al., Identification of a second human subtilisin-like protease gene in the fes/fps region of chromosome 15, *DNA Cell Biol.* 10:757-69 (1991).

(Continued)

Primary Examiner — Ganapathirama Raghu
(74) *Attorney, Agent, or Firm* — Marshall, Gerstein & Borun LLP

(57) ABSTRACT

The present invention relates to recombinant furin (rFurin) and methods for producing rFurin. More specifically, the invention relates to substantially animal protein-free rFurin and methods for producing substantially animal protein-free rFurin.

12 Claims, 18 Drawing Sheets

(56) References Cited

OTHER PUBLICATIONS

Kisselev et al., Polypeptide release factors in prokaryotes and eukaryotes: Same function, different structure. *Structure* 10: 8-9 (2002).

Klimpel et al., Anthrax toxin protective antigen is activated by a cell surface protease with the sequence specificity and catalytic properties of furin, *Proc. Natl. Acad. Sci.* USA 89:10277-81 (1992).

Leduc et al., Activation of human furin precursor processing endoprotease occurs by an intramolecular autoproteolytic cleavage, *J. Biol. Chem.* 267:14304-8 (1992).

Molloy et al., Human furin is a calcium-dependent serine endoprotease that recognizes the sequence Arg-X-X-Arg and efficiently cleaves anthrax toxin protective antigen, *J. Biol. Chem.* 267:16396-402 (1992).

Nakayama et al., Identification of the fourth member of the mammalian endoprotease family homologous to the yeast Kex2 protease. Its testis-specific expression, *J. Biol. Chem.* 267:5897-900 (1992).

Oda et al., Proteolytic cleavages of proalbumin and complement Pro-C3 in vitro by a truncated soluble form of furin, a mammalian homologue of the yeast Kex2 protease, *Biochem. Biophys. Res. Commun.* 189:1353-61 (1992).

Preininger et al., Strategies for recombinant Furin employment in a biotechnological process: complete target protein precursor cleavage, *Cytotechnology* 30:1-16 (1999).

Rehemtulla et al., Preferred sequence requirements for cleavage of pro-von Willebrand factor by propeptide-processing enzymes, *Blood* 79:2349-55 (1992).

Rehemtulla et al., Regulation of PACE propeptide-processing activity: requirement for a post-endoplasmic reticulum compartment and autoproteolytic activation, *Proc. Natl. Acad. Sci.* USA 89:8235-9 (1992).

Roebroek et al., Characterization of human c-fes/fps reveals a new transcription unit (fur) in the immediately upstream region of the proto-oncogene, *Mol. Biol. Rep.* 11:117-25 (1986).

Roebroek et al., Evolutionary conserved close linkage of the c-fes/fps proto-oncogene and genetic sequences encoding a receptor-like protein, EMBO J. 5:2197-202 (1986).

Schlokat et al., Production of highly homogeneous and structurally intact recombinant von Willebrand factor multimers by furin-mediated propeptide removal in vitro, *Biotechnol. Appl. Biochem.* 24:257-67 (1996).

Seffernick et al., Melamine deaminase and Atrazine chlorohydrolase: 98 percent identical but functionally different. *J. Bacteriol.* 183(8): 2405-10 (2001).

Smeekens et al., Identification of a cDNA encoding a second putative prohormone convertase related to PC2 in AtT20 cells and islets of Langerhans, *Proc. Natl. Acad. Sci. USA* 88:340-4 (1991).

Smeekens et al., Identification of a human insulinoma cDNA encoding a novel mammalian protein structurally related to the yeast dibasic processing protease Kex2, *J. Biol. Chem.* 265:2997-3000 (1990).

Stieneke-Grober et al., Influenza virus hemagglutinin with multibasic cleavage site is activated by furin, a subtilisin-like endoprotease, *EMBO J.* 11:2407-14 (1992).

Tsuneoka et al., Evidence for involvement of furin in cleavage and activation of diphtheria toxin, *J. Biol. Chem.* 268:26461-5 (1993).

Turecek et al., Biochemical and functional characterization of a serum-free rVWF drug candidate, *Blood, ASH Annual Meeting Abstracts* 108: 303A, Abstract 1017 (2006).

Van De Ven et al., Furin is a subtilisin-like proprotein processing enzyme in higher eukaryotes, *Mol. Biol. Rep.* 14:265-75 (1990).

Van De Ven et al., Structure and function of eukaryotic proprotein processing enzymes of the subtilisin family of serine proteases, *Crit. Rev. Oncog.* 4:115-36 (1993).

Van Den Ouweland et al., Nucleotide sequence analysis of the human fur gene, *Nucleic Acids Res.* 17:7101-2 (1989).

Van Den Ouweland et al., Structural homology between the human fur gene product and the subtilisin-like protease encoded by yeast KEX2, *Nucleic Acids Res.* 18:664 (1990).

Verweij et al., Full-length von Willebrand factor (vWF) cDNA encodes a highly repetitive protein considerably larger than the mature vWF subunit, *EMBO J.* 5:1839-47 (1986).

Vey et al., Maturation of the trans-Golgi network protease furin: compartmentalization of propeptide removal, substrate cleavage, and COOH-terminal truncation, *J. Cell Biol.* 127:1829-42 (1994).

Vidricaire et al., Characterization of a secreted form of human furin endoprotease, *Biochem. Biophys. Res. Commun.* 195:1011-8 (1993).

Wasley et al., PACE/furin can process the vitamin K-dependent profactor IX precursor within the secretory pathway, *J. Biol. Chem.* 268:8458-65 (1993).

Whisstock et al., Prediction of protein function from protein sequence, *Q. Rev. Biophys.* 36(3):307-40 (2003).

Wise et al., Expression of a human proprotein processing enzyme: correct cleavage of the von Willebrand factor precursor at a paired basic amino acid site, *Proc. Natl. Acad. Sci.* USA 87:9378-82 (1990).

Witkowski eta I., Conversion of b-ketoacyl synthase to a malonyl decarboxylase by replacement of the active cystein with glutamine, *Biochemistry* 38:11643-50 (1999).

Nishigori et al., Proinsulin cleaved by furin is processed to chromatographically mature insulin by carboxypeptidases in non-neuroendocrine cells, *Peptides* 17(5):789-95 (1996).

International Search Report and Written Opinion of the International Searching authority, PCT/US2008/087732, dated May 8, 2009.

Rasmussen et al., Isolation, characterization and recombinant protein expression in Veggie-CHO: A serum-free CHO host cell line, *Cytotech.* 28:31-42 (1998).

Nakayama, Purification of recombinant soluble forms of furin produced in Chinese hamster ovary cells. *Methods Enzymol.* 244: 167-75 (1994).

* cited by examiner

Comments to FACS results

| Cell population | Sample code | % Furin positive | Mean | Median |
|---|---|---|---|---|
| Control | CHO DUKX DXB11neg | 0.25 | 2.52 | 2.37 |
| PMCB#01 | RE06-076-07 | 74.06 | 12.55 | 11.55 |
| Irrelevant sample | RE06-077-07 | 81.02 | 17.59 | 15.96 |
| PMCB#04 | RE06-079-07 | 80.74 | 13.71 | 12.41 |
| Irrelevant sample | SK06-63-28 | 67.89 | 10.22 | 8.35 |

The samples were analyzed by SDS-PAGE on 8% gels. The separated polypeptides were visualized by silver staining ORFU06002:
Lane 1: MMC 01
Lane 2: MMC 02
Lane 3: MMC 03
Lane 4: MMC 04
Lane 5: MMC 05
Lane 6: MMC 06
Lane 7: MMC 07
Lane 8: MMC 08

ORFU07002:
Lane 9: MMC 01
Lane 10: MMC 02
Lane 11: MMC 03
Lane 12: MMC 04
Lane 13: MMC 05
Lane 14: MMC 06

The samples were analyzed by SDS-PAGE on 8% gels. The separated polypeptides were visualized by Western blot, using a monoclonal Goat-anti Furin antibody (Alexis Mon-148) as first antibody.

ORFU06002:

Lane 1: MMC 01
Lane 2: MMC 02
Lane 3: MMC 03
Lane 4: MMC 04
Lane 5: MMC 05
Lane 6: MMC 06
Lane 7: MMC 07
Lane 8: MMC 08

ORFU07002:

Lane 9: MMC 01
Lane 10: MMC 02
Lane 11: MMC 03
Lane 12: MMC 04
Lane 13: MMC 05
Lane 14: MMC 06

The samples were analyzed on vertical IEF using a pH gradient of PH 7.0 – pH 3.0. The separated polypeptides were visualized by Western blotting using a monoclonal Goat-anti Furin antibody (Alexis Mon-148) as first antibody.

ORFU06002:

Lane 1: MMC 01

Lane 2: MMC 02

Lane 3: MMC 03

Lane 4: MMC 04

Lane 5: MMC 05

Lane 6: MMC 06

Lane 7: MMC 07

Lane 8: MMC 08

The samples were analyzed by vertical IEF pH 7.0 – 3.0. The separated polypeptides were visualized by Coomassie staining.

ORFU07002:

Lane 1: MMC 01

Lane 2: MMC 02

Lane 3: MMC 03

Lane 4: MMC 04

Lane 5: MMC 05

Lane 6: MMC 06

The samples were analyzed by vertical IEF pH 7.0 – 3.0. The separated polypeptides were visualized by Western blotting, using a monoclonal Goat-anti Furin antibody (Alexis Mon-148) as first antibody.

ORFU07002:

Lane 1: MMC 01

Lane 2: MMC 02

Lane 3: MMC 03

Lane 4: MMC 04

Lane 5: MMC 05

Lane 6: MMC 06

US 9,127,264 B2

SUBSTANTIALLY ANIMAL PROTEIN-FREE RECOMBINANT FURIN AND METHODS FOR PRODUCING THE SAME

This application is a continuation of U.S. application Ser. No. 12/339,597, filed Dec. 19, 2008, now abandoned, which claims priority benefit of U.S. Provisional Application No. 61/108,152, filed Dec. 31, 2007, which are incorporated by reference herein in their entirety.

FIELD OF THE INVENTION

The present invention generally relates to recombinant furin (rFurin) and methods for producing rFurin. More specifically, the invention relates to substantially animal protein-free rFurin and methods for producing substantially animal protein-free rFurin.

BACKGROUND OF THE INVENTION

Active or mature proteins are usually present in very low amounts in living organisms. Therefore, their pro-proteins or pro-enzymes are preferably activated in vitro by contacting them with activation enzymes (e.g. proteases). Pro-proteins (or protein precursors) are inactive proteins that become active by one or more posttranslational modifications and, in particular, by the cleavage of a pro-peptide from the pro-protein. Examples of pro-proteins include, for example, pro-insulin, prothrombin, pro-von Willebrand Factor (pro-VWF), and the like.

Von Willebrand factor (VWF) is a blood glycoprotein involved in coagulation. VWF is deficient or defective in von Willebrand disease and is involved in a large number of other diseases, including thrombotic thrombocytopenic purpura, Heyde's syndrome, and possibly hemolytic-uremic syndrome. VWF is a glycoprotein circulating in plasma as a series of multimers ranging in size from about 500 to 20,000 kD. Multimeric forms of VWF are composed of 250 kD polypeptide subunits linked together by disulfide bonds. VWF mediates the initial platelet adhesion to the sub-endothelium of the damaged vessel wall, and it is believed that only the larger multimers of VWF exhibit hemostatic activity. VWF multimers having large molecular masses are stored in the Weibel-Pallade bodies of endothelial cells and are liberated upon stimulation. Liberated VWF is then further processed by plasma proteases to result in low molecular weight forms of VWF.

In humans the removal of the pro-peptide is almost complete, whereas, in mammalian cell lines with a high level of recombinant VWF expression, this process is not very efficient. Therefore, cell culture supernatants from such recombinant cell lines usually comprise a mixture of mature VWF and VWF precursors, like pro-VWF. In order to obtain mature VWF, it is therefore necessary to convert the VWF precursors, in particular pro-VWF, into mature VWF. This process is usually achieved by cleaving the pro-peptide with a protease.

Current conventional methods produce mature VWF by either incubating its pro-form with proteases in a liquid phase, whereby the maturation itself (i.e., the cleavage of the pro-peptide from the pro-protein) occurs in an unbound state in free solution, or as described, for example, in WO 00/49047, by immobilizing the protease on a solid carrier, which is contacted and incubated with a preparation comprising pro-VWF (see e.g. WO 00/49047). However, these methods comprise various disadvantages over the methods according to the present invention.

Industrially, VWF and, in particular, recombinant VWF (rVWF) is synthesized and expressed together with recombinant Factor VIII (rFVIII) in a genetically engineered Chinese Hamster ovary (CHO) cell line. The function of the co-expressed rVWF is to stabilize rFVIII in the cell culture process. rVWF is synthesized in the cell in the pro-form, containing a large pro-peptide attached to the N-terminus. Upon maturation in the endoplasmic reticulum and Golgi apparatus, the pro-peptide is cleaved by the action of the cellular protease furin and the mature protein is secreted as a homopolymer of identical subunits, consisting of dimers of the expressed protein. However, the maturation is typically incomplete, leading to a product comprising a mixture of pro-VWF and mature VWF.

Previous publications have shown that pro-VWF can be converted to mature VWF by in vitro treatment with furin or furin-like proteases (Schlokat et al., *Biotechnol. Appl. Biochem.* 24: 257-267, 1996; Preininger et al., *Cytotechnology* 30: 1-15, 1999; and EP 0775750A). In particular, EP 0775750A suggests the co-expression of furin and VWF recombinantly so that the maturation of VWF may occur in situ.

Recombinant furin (rFurin) transforms pro-rVWF (pro-recombinant von Willebrand factor) to rVWF by cleaving the Arg741-Ser742 peptide bond. This maturation step is part of a rVWF production process for the treatment of von Willebrand Disease Type B and part of the manufacturing process for recombinant Factor VIII-half life (rFVIII-HL). Furin belongs to the family of the pro-protein convertases and is dependent on calcium ($Ca^{2+}$). Furin specifically cleaves the C-terminal peptide bond of arginine within a specific sequence, containing arginine at positions −1 and −4. This sequence can be found in numerous human proteins, showing that furin plays a major role in the maturation of a number of human pro-proteins.

The production of activated proteins is of high clinical and diagnostic importance. For example, active or mature proteins, like mature VWF, may be used to control blood coagulation. The present invention provides improved recombinant furin (rFurin) which is substantially animal protein-free rFurin for the subsequent production of activated proteins. More specifically, the present invention provides substantially animal protein-free rFurin for transforming pro-VWF into mature VWF.

SUMMARY OF THE INVENTION

The present invention provides recombinant furin (rFurin), which is substantially animal protein-free recombinant furin (rFurin), and methods for producing same. Such rFurin is substantially free of other proteins which may normally be associated with the production of rFurin, such as serum proteins and host cell proteins. This rFurin allows for the subsequent production of mature proteins with high specific activity and high purity without side effects associated with protein contaminant in the rFurin preparation. More specifically, this rFurin allows for the production of mature VWF with high specific activity and high purity. Accordingly, the invention provides methods for selection and adaptation of recombinant host cells to chemically-defined medium, expression of rFurin which is secreted into cell culture supernatant, and purification of rFurin after cell removal.

The substantially animal protein-free rFurin of the invention includes preparations or compositions of rFurin comprising host cell protein in a concentration which ranges between about 0.1 to 0.6 ng protein or less/Unit furin activity or between about 2 and 11 µg protein or less/mL and essentially lacking contaminating proteins from serum in the culture medium. In one aspect, the substantially animal protein-free rFurin encompasses preparations of rFurin comprising contaminating host cell DNA in a concentration between about 0 to 0.4 pg DNA or less/Unit furin activity or between about 0 and 24 ng DNA or less/mL and essentially lacking contaminating proteins from serum in the culture medium.

The invention includes compositions comprising substantially animal protein free recombinant furin at an activity of at least 10000 U furin/mL and host cell protein at a concentration less than about 11 µg protein/mL. Such compositions may also comprise host cell protein at a concentration less than about 1.0 ng protein/U furin activity. In one aspect, the host cell protein is from a CHO cell.

In another aspect, the invention includes compositions comprising substantially animal protein free recombinant furin at an activity of at least 10000 U furin/mL and host cell DNA at a concentration less than about 14 ng DNA/mL. In various aspects, such compositions also comprise host cell DNA at a concentration less than about 0.5 pg DNA/U furin activity. In one aspect, the host cell DNA is from a CHO cell.

The invention also includes compositions comprising substantially animal protein free recombinant furin at a specific furin activity of at least about 100 U/µg and host cell protein at a concentration less than about 11 µg protein/mL. Such compositions may also comprise host cell protein at a concentration less than about 1.0 ng protein/U furin activity. In one aspect, the host cell protein is from a CHO cell.

The invention further includes compositions comprising substantially animal protein free recombinant furin at a specific furin activity of at least about 100 U/µg and host cell DNA at a concentration less than about 14 ng DNA/mL. Such compositions may also comprise host cell DNA at a concentration less than about 0.5 pg DNA/U furin activity. In one aspect, the host cell DNA is from a CHO cell.

The invention also includes methods of making a composition comprising substantially animal protein-free recombinant furin described herein. Such methods comprise the step of adapting the host cells to growth in medium with increasingly lower concentrations of serum until all serum is removed from the medium. In another aspect, the methods comprise the step of transferring the host cell from growth in medium comprising serum to growth in serum-free medium. In an exemplary aspect, the host cell is a CHO cell.

The invention includes methods of using a composition comprising substantially animal protein-free recombinant furin described herein. Such uses comprise the step of contacting a pro-protein with the composition under conditions to cleave a pro-peptide from the pro-protein to form a mature protein. The rFurin can be used in the formation of any mature protein from a pro-protein that is cleaved by furin. In one aspect, the mature protein is von Willebrand Factor. In another aspect, the mature protein is Factor VIII. In addition, the invention contemplates that the rFurin of the invention is useful for both in vitro and in vivo processing of any pro-protein that it cleaves.

BRIEF DESCRIPTION OF THE DRAWING

A further illustration of the invention is given with reference to the accompanying drawings, which are set out below in FIGS. 1-18.

DETAILED DESCRIPTION OF THE INVENTION

Figure 1:
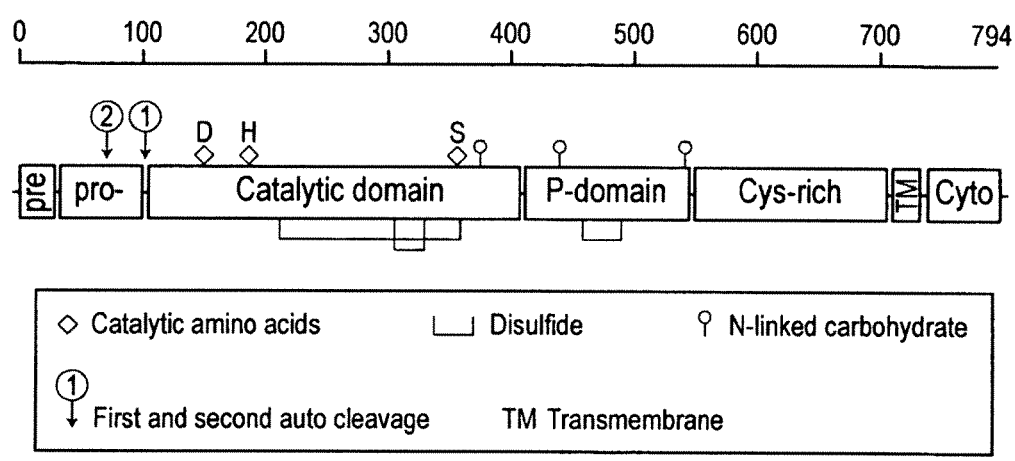
FIG. 1 depicts the expressed active rFurin protease construct in one embodiment of the invention. The rFurin construct is truncated at the C-terminal end at AA 577 to remove the Cys-rich transmembrane and cytosol domains.

The present invention relates to the development and production of a recombinant host cell line that is capable of growing in serum-free medium and secreting active recombinant furin (rFurin) into the cell culture supernatant. The host cell line selected for transfection of a plasmid encoding recombinant furin is in one aspect the same as used for expression of recombinant Factor VIII and recombinant VWF. The resulting rFurin is then purified so that is substantially free of animal protein.

Furin, also known as PACE, PACE4, PC1/PC3, PC2, PC4 and PC5/PC6, belongs to the group of the subtilisin-like serine proteases, which play an important role in the cleavage of proproteins, especially in the secretory synthesis (Van de Ven et al., *Crit. Rev. Oncogen.* 4:115-136, 1993). Pro-proteins are post-translationally, intracellularily processed to their mature form by the endogenous protease in the Golgi apparatus. The protease cleavage site comprises a recognition sequence which is characterized by the amino acid sequence Arg-X-Lys/Arg-Arg. The protease furin cleaves proproteins specifically after this consensus sequence (Hosaka et al., *J. Biol. Chem.* 266:12127-12130, 1991).

The DNA and amino acid sequence of human and murine furin, as well as further proteins with subtilisin-like protease function have been identified (Roebroek et al., *Mol. Biol. Rep.* 11: 117-125, 1986; Roebroek et al., *EMBO J.* 5:2197-2202, 1986; Barr et al., *DNA Cell Biol.* 10:319-328, 1991; Van den Ouweland et al., *Nucleic Acids Res.* 17:7101-7102, 1989; Van den Ouweland et al., *Nucleic Acids Res.* 18:664, 1990; Smeekens et al., 1990, *J. Biol. Chem.* 265:2997-3000; Smeekens et al., *Proc. Natl. Acad. Sci. USA.* 88; 340-344, 1991; Kiefer et al., *DNA Cell Biol.* 10: 757, 1991; Nakayama et al., *J. Biol. Chem.* 267:5897-5900, 1992; and Hatsuzawa et al., *J. Biol. Chem.* 265: 22075-22078, 1990). The human furin gene encodes a protein consisting of 794 amino acids, certain functions being allocatable to individual characteristic regions: a catalytic center, a middle domain, a cystine-rich region, a transmembrane domain, and a cytoplasmatic domain (Van de Ven et al., *Crit. Rev. Oncogen.* 4:115-136, 1993). In one aspect, the human furin polypeptide is set out in GenBank Accession No: EAX02111 (National Center for Biotechnology Information, U.S. National Library of Medicine, Bethesda, Md.). However, the worker of ordinary skill in the art will appreciate that any protein having furin biological activity, i.e., the ability to cleave pro-proteins (e.g., pro-VWF to produce mature VWF) can be produced by the methods described herein.

Intact furin is incorporated into the membrane system of the Golgi apparatus where it is functionally active (Bresnahan et al., *J. Cell Biol.* 111:2851-2859, 1990). A truncated form of the over-expressed native furin of 75-80 kD could be detected in cell supernatant as secreted protein (Wise et al., *Proc. Natl. Acad. Sci. USA* 87: 9378-9382, 1990). This naturally secreted furin is known as "shed furin" (Vidricaire et al., *Biochem. Biophys. Res. Comm.* 195:1011-1018, 1993) and is cleaved N-terminally of the transmembrane portion (Vey et al., *J. Cell Biol.* 127:1829-1842, 1994).

Furin truncated by genetic engineering, in which the encoding part of the transmembrane and cytoplasmatic domains has been deleted, can also be expressed and secreted correspondingly. Such N-terminal deletions have been described for amino acids 714-794 (Leduc et al., *J. Biol. Chem.* 267:14304-14308, 1992, Molloy et al., *J. Biol. Chem.* 267:16396-16402, 1992); for amino acids 716-794 ("Sol-PACE") (Wasley et al., *J. Biol. Chem.* 268:8458-8465, 1993; and Rehemtulla et al., *Blood* 79:2349-2355, 1992); and for amino acids 705-794 (Hatsuzawa et al., *J. Biol. Chem.* 267: 16094-16099, 1992). Furin mutants additionally comprising a deletion of the cystine-rich region have also been described (Hatsuzawa et al., *J. Biochem.* 101:296-301, 1992; Creemers et al., *J. Biol. Chem.* 268:21826-21834, 1993).

The endoproteolytic activity of furin and its selectivity for basic amino acids was first determined in experiments with pro-von Willebrand factor (pro-vWF). Pro-vWF consists of a propolypeptide with 741 amino acids and mature von Willebrand factor (vWF) with 2050 amino acids (Verweij et al., *EMBO J.* 5:1839-1847, 1986). The liberation of mature vWF from pro-vWF results from a proteolytic cleavage after Arg763. Transfection of pro-vWF cDNA in eukaryotic expression vectors results in the production of equimolar amounts of the 360 kD pro-vWF and of the 260 kD mature vWF in the cell culture supernatant. vWF is probably processed into its mature form in transfected cells, by endogenously occurring furin (Wise et al., *Proc. Natl. Acad. Sci. USA* 87:9378-9382, 1990, Van de Ven et al., *Mol. Biol. Rep.* 14:265-275, 1990).

Among additional pro-proteins which are cleaved by furin or by subtilisin-like enzymes, respectively, are a series of hormones and growth factors (e.g., proactivin A, hepatocyte-growth factor), plasma proteins (albumin, factor VII, factor IX, factor X), receptors (insulin pro-receptor), viral proteins (e.g. HIV-1 gp160, influenza virus haemagglutinin) as well as bacterial proteins (diphteria toxin, anthrax toxin) (Decroly et al., *J. Biol. Chem.* 269:12240-12247, 1994; Stieneke-Grober et al., *EMBO J.* 11:2407-2414, 1992; Barr, *Cell* 66:1-3, 1991, Wasley et al., *J. Biol. Chem.* 268:8458-8465, 1993; Klimpel et al., *Proc. Natl. Acad. Sci. USA* 89:10277-10281, 1992; Tsuneoka et al., *J. Biol. Chem.* 268:26461-26465, 1993; Bresnahan et al., *J. Cell. Biol.* 111:2851-2859, 1990; Hosaka et al., *J. Biol. Chem.* 266:12127-12130, 1991; and Vey et al., *J. Cell. Biol.* 127:1829-1842, 1994). The rFurin of the present invention is contemplated for use in cleaving these pro-proteins as well.

By co-expression of the nucleic acid sequences encoding intact furin and a pro-protein in eukaryotic cell cultures, an increased processing of the pro-proteins has been achieved in vivo. This has been demonstrated, e.g., for pro-factor IX (Wasley et al., *J. Biol. Chem.* 268:8458-8465, 1993) and for pro-vWF (WO 91/06314; Van de Ven et al., *Mol. Bio. Rep.* 14:265-275, 1990; and Rehemtulla et al., *Blood* 79:2349-2355, 1992). The present invention contemplates that the rFurin of the invention is useful for both in vitro and in vivo processing of any pro-protein that it cleaves.

Beside the co-expression of intact furin with pro-proteins, truncated furin has been expressed together with pro-proteins. Furin deletion mutants have been demonstrated as enzymatically active when co-expressed in vivo and as secreted; the enzymatic activity of such deletion mutants could be detected inter alia in the processing of pro-factor IX (Wasley et al., *J. Biol. Chem.* 268:8458-8465, 1993) and pro-vWF (Rehemtulla et al., *Blood* 79: 2349-2355, 1992). Co-expression experiments with furin deletion mutants have shown that the transmembrane and the cytoplasmatic parts of the protein are not essential to the catalytic function (Rehemtulla et al., *Proc. Natl. Acad. Sci. USA* 89: 8235-8239, 1992).

WO 91/06314 discloses the recombinant expression of furin in prokaryotic and eukaryotic cells, the preparation of furin fusion proteins, deletion mutants and fragments, the purification of recombinantly prepared furin, and the potential use of purified furin for the processing of proproteins in vitro in general. WO 92/09698 describes the expression of PACE (furin), the co-expression with inactive precursors of proteins, such as, e.g., pro-vWF, as well as the preparation of fusion proteins. Stieneke-Grober et al. (*EMBO J.* 11:2407-2414, 1992) describe the in vitro cleavage of influenza virus HA protein by means of purified furin. Decroly et al. (*J. Biol.*

*Chem.* 269:12240-12247, 1994) describe the in vitro cleavage of HIV gp160 by means of furin.

In experiments with C-terminally shortened furin, the cleavage of pro-albumin and complement Pro-C3 (Oda et al., *Biochem. Biophys. Res. Commun.* 189:1353-1361, 1992), anthrax toxin (Klimpel et al., *Proc. Natl. Acad. Sci. USA* 89:10277-10281, 1992), diphtheria toxin (Tsuneoka et al., *J. Biol. Chem.* 268: 26461-26465, 1993) and pro-factor IX (Wasley et al., *J. Biol. Chem.* 268:8458-8468, 1993, Bristol et al., *Biochemistry* 33:14136-14143, 1994) has been carried out successfully in vitro.

The rFurin of the present invention, therefore, is contemplated for use in the in vivo and in vitro processing of pro-proteins as described above. In one aspect, the rFurin of the invention is especially useful in the in vitro processing of pro-VWF and pro-factor IX. However, its use is not to be construed as limited to the processing of said proteins. In a further aspect the rFurin of the invention is particularly useful in the in vitro processing of recombinant pro-proteins.

A further aspect of the present invention is the co-culturing of cells which express pro-vWF and rFurin. Thus, pro-vWF in the cell culture supernantant is cleaved in vitro into its active form by rFurin which is also present in the cell culture supernatant. Processed vWF is subsequently isolated from the culture and purified, as discussed in U.S. Pat. No. 6,210,929, incorporated herein by reference. For co-culturing, all the common expression systems can be used, and various systems for expressing pro-vWF and rFurin may be combined with each other. In one aspect, an expression system is used in which both pro-vWF and rFurin are expressed in host cells of the same origin.

The term "host cell" is used to refer to a cell which has been transformed, or is capable of being transformed with a nucleic acid sequence and then of expressing a selected gene of interest. The term includes the progeny of the parent cell, whether or not the progeny is identical in morphology or in genetic make-up to the original parent, so long as the selected gene is present.

The invention includes any host cells or hosts known in the art for recombinant protein production. Therefore, the cells in the present invention can be derived from any source. In one aspect, the invention includes eukaryotic and prokaryotic host cells. In another aspect, the invention includes plant cells, animal cells, fish cells, amphibian cells, avian cells, insect cells, and yeast cells. In one aspect, exemplary yeast cells include *Pichia*, e.g. *P. pastoris*, and *Saccharomyces* e.g. *S. cerevisiae*, as well as *Schizosaccharomyces pombe, Kluyveromyces, K. Zactis, K. fragilis, K. bulgaricus, K. wickeramii, K. waltii, K. drosophilarum, K. thernotolerans*, and *K. marxianus; K. yarrowia; Trichoderma reesia, Neurospora crassa, Schwanniomyces, Schwanniomyces occidentalis, Neurospora, Penicillium, Totypocladium, Aspergillus, A. nidulans, A. niger, Hansenula, Candida, Kloeckera, Torulopsis*, and *Rhodotorula*. Exemplary insect cells include *Autographa californica* and *Spodoptera frugiperda*, and *Drosophila*.

In a further aspect, the host cells are mammalian cells, including primary epithelial cells (e.g., keratinocytes, cervical epithelial cells, bronchial epithelial cells, tracheal epithelial cells, kidney epithelial cells and retinal epithelial cells) and established cell lines and their strains (e.g., 293 embryonic kidney cells, BHK cells, HeLa cervical epithelial cells and PER-C6 retinal cells, MDBK (NBL-1) cells, 911 cells, CRFK cells, MDCK cells, CHO cells, BeWo cells, Chang cells, Detroit 562 cells, HeLa 229 cells, HeLa S3 cells, Hep-2 cells, KB cells, LS 180 cells, LS 174T cells, NCI-H-548 cells, RPMI 2650 cells, SW-13 cells, T24 cells, WI-28 VA13, 2RA cells, WISH cells, BS-C-I cells, LLC-MK$_2$ cells, Clone M-3 cells, 1-10 cells, RAG cells, TCMK-1 cells, Y-1 cells, LLC-PK$_1$ cells, PK(15) cells, GH$_1$ cells, GH$_3$ cells, L2 cells, LLC-RC 256 cells, MH$_1$C$_1$ cells, XC cells, MDOK cells, VSW cells, and TH-I, B1 cells, or derivatives thereof), fibroblast cells from any tissue or organ (including but not limited to heart, liver, kidney, colon, intestines, esophagus, stomach, neural tissue (brain, spinal cord), lung, vascular tissue (artery, vein, capillary), lymphoid tissue (lymph gland, adenoid, tonsil, bone marrow, and blood), spleen, and fibroblast and fibroblast-like cell lines (e.g., Chinese hamster ovary (CHO) cells, TRG-2 cells, IMR-33 cells, Don cells, GHK-21 cells, citrullinemia cells, Dempsey cells, Detroit 551 cells, Detroit 510 cells, Detroit 525 cells, Detroit 529 cells, Detroit 532 cells, Detroit 539 cells, Detroit 548 cells, Detroit 573 cells, HEL 299 cells, IMR-90 cells, MRC-5 cells, WI-38 cells, WI-26 cells, MiCl$_1$ cells, CV-1 cells, COS-1 cells, COS-3 cells, COS-7 cells, Vero cells, DBS-FrhL-2 cells, BALB/3T3 cells, F9 cells, SV-T2 cells, M-MSV-BALB/3T3 cells, K-BALB cells, BLO-11 cells, NOR-10 cells, C.sub.3H/IOTI/2 cells, HSDM$_1$C$_3$ cells, KLN205 cells, McCoy cells, Mouse L cells, Strain 2071 (Mouse L) cells, L-M strain (Mouse L) cells, L-MTK (Mouse L) cells, NCTC clones 2472 and 2555, SCC-PSA1 cells, Swiss/3T3 cells, Indian muntjac cells, SIRC cells, C.sub.II cells, and Jensen cells, or derivatives thereof).

Exemplary mammalian cells include varieties of CHO, BHK, HEK-293, NS0, YB2/3, SP2/0, and human cells such as PER-C6 or HT1080, as well as VERO, HeLa, COS, MDCK, NIH3T3, Jurkat, Saos, PC-12, HCT 116, L929, Ltk-, W138, CV1, TM4, W138, Hep G2, MMT, a leukemic cell, an embryonic stem cell or a fertilized egg cell. In one aspect of the invention, an exemplary host cell is a CHO cell. In a further aspect of the invention, the medium is used to culture CHO cells in suspension.

Host cells can be engineered to express a protein in a variety of ways known in the art, including but not limited to insertion of exogenous nucleic acid encoding the desired protein, optionally as part of an expression vector, insertion of an exogenous expression control sequence such that it causes increased expression of the host cell's endogenous gene encoding the desired protein, or activation of the host cell's endogenous expression control sequence(s) to increase expression of endogenous gene encoding the desired protein.

Cultures of host cells can be prepared according to any methods known in the art, and methods of growing such host cells and recovering recombinant protein produced by the cells, whether from the cells or culture medium, are known in the art. Such culturing methods may involve addition of chemical inducers of protein production to the culture medium. Exemplary host cells and procedures are described below.

A nucleic acid encoding a furin polypeptide is inserted into an appropriate expression vector using standard molecular biology techniques. In one aspect, the nucleic acid encodes the human furin polypeptide as set out in GenBank Accession No: EAX02111 (National Center for Biotechnology Information, U.S. National Library of Medicine, Bethesda, Md.), however the worker of ordinary skill in the art will appreciate that any protein having furin biological activity, i.e., the ability to cleave pro-VWF to produce mature VWF, can be produced by the methods described herein. In a further aspect, a C-terminally truncated, fully secreted rFurin was designed by deleting nucleotides encoding amino acids 578 to 794 comprising the cystine-rich, the transmembrane, and the cytoplasmic domains. In an even further aspect, a tail of amino acids may be added to aid in purification processes. In yet another aspect, a tail of 10 histidine residues was added after amino acid 577, with or without interjacent four glycine residues serving as a flexible linker.

Expression vectors optionally may include a promoter, one or more enhancer sequences, an origin of replication, a transcriptional termination sequence, a complete intron sequence containing a donor and acceptor splice site, a sequence encoding a leader or signal sequence for polypeptide secretion, a ribosome binding site, a polyadenylation sequence, a polylinker region for inserting the nucleic acid encoding the polypeptide to be expressed, and/or a selectable marker element. Each of these sequences is discussed below.

Optionally, the vector may contain a "tag"-encoding sequence, i.e., an oligonucleotide sequence located at the 5' or 3' end of the furin polypeptide coding sequence; the oligonucleotide molecule encodes polyHis (such as hexaHis), or another "tag" such as FLAG, HA (hemaglutinin influenza virus) or myc for which commercially available antibodies exist. This tag is typically fused to the polypeptide upon expression of the polypeptide, and can serve as a means for detection or affinity purification of the furin polypeptide from the host cell.

Suitable vectors include, but are not limited to, cosmids, plasmids, or modified viruses, but it will be appreciated that the vector system must be compatible with the selected host cell. In one aspect, the vector is a plasmid. In a further aspect, the plasmid is pUC-based cloning vector. Other vectors that can be used in the invention include expression vectors, replication vectors, probe generation vectors, sequencing vectors, and retroviral vectors. Vectors contemplated by the invention include, but are not limited to, microorganisms such as bacteria transformed with recombinant bacteriophage, plasmid, phagemid, or cosmid DNA expression vectors; yeast transformed with yeast expression vectors; insect cell systems infected with viral expression vectors (e.g., baculovirus); plant cell systems transfected with virus expression vectors (e.g., Cauliflower Mosaic Virus, CaMV; Tobacco Mosaic Virus, TMV) or transformed with bacterial expression vectors (e.g., Ti or pBR322 plasmid); or even animal cell systems.

Mammalian expression vectors typically comprise an origin of replication, a suitable promoter, and also any necessary ribosome binding sites, polyadenylation site, splice donor and acceptor sites, transcriptional termination sequences, and 5' flanking nontranscribed sequences. DNA sequences derived from the SV40 viral genome, for example, the SV40 origin, early promoter, enhancer, splice, and polyadenylation sites may be used to provide the required expression control elements. Exemplary eukaryotic vectors include pcDNA3, pWLneo, pSV2cat, pOG44, PXTI, pSG (Stratagene) pSVK3, pBPV, pMSG, pSVL, and pVITRO3.

Nucleic acid can be transferred into host cells by any means known in the art, e.g. through liposome-mediated transfer, receptor-mediated transfer (ligand-DNA complex), electroporation, microinjection of DNA, cell fusion. DEAE-dextran, calcium chloride, calcium phosphate precipitation, microparticle bombardment, infection with viral vectors, lipofection, transfection, or homologous recombination.

The term "transformed" or "transfected" as used herein refers to a host cell modified to contain an exogenous polynucleotide, which can be integrated into the chromosome of the host cell or maintained as an episomal element. It is contemplated that in certain aspects of the methods provided, the host cell is transfected in a "transfection step." The method may comprise multiple transfection steps. In addition, other methods known in the art for introducing exogenous polynucleotides into a host cell, including for example, electroporation and cell fusion which are not technically "transformation" are within the definition of the term "transformation" for purposes of this description.

The invention also provides methods for culturing, i.e. growing, host cells under conditions that result in rFurin protein expression. Such methods include the step of recovering the rFurin produced by the host cells from the culture medium. In an exemplary aspect, the host cells are grown in a chemically defined, serum-free medium. Because serum is a biochemically undefined material, contains many components which have not been fully identified, differs from lot to lot, and is frequently contaminated with microorganisms, such as viruses and mycoplasma, the presence of serum in the recombinant production of rFurin is undesirable. Furthermore, the presence of animal proteins in serum in the culture media can require lengthy purification procedures.

The invention therefore provides a biochemically defined culture medium, essentially free from animal protein, for culturing cells recombinantly transfected with a human furin gene. The components of the medium are mostly inorganic, synthetic or recombinant and as such are not obtained directly from any animal source.

The cell culture medium of the present invention may comprise one or more replacement compounds and can comprise one or more replacement compounds which can be metal binding compounds and/or can comprise one or more complexes comprising one or more replacement compounds. In some embodiments, the medium can comprise one or more complexes, said complex comprising one or more transition elements or salts or ions thereof complexed one or more replacement compounds which can be metal-binding compounds. In some embodiments, the medium is capable of supporting the culture of cells in vitro and permits transfection of cells cultured therein.

According to one aspect of the invention, a transition element is preferably selected from the group consisting of scandium, titanium, vanadium, chromium, manganese, iron, cobalt, nickel, copper, zinc, yttrium, zirconium, niobium, molybdenum, technetium, rubidium, rhodium, palladium, silver, cadmium, lanthanum, hafnium, tantalum, tungsten, rhenium, osmium, iridium, platinum, gold, mercury, and actinium, or salts or ions thereof, and is preferably an iron salt. Suitable iron salts include, but are not limited to, $FeCl_3$, $Fe(NO_3)_3$ or $FeSO_4$ or other compounds that contain $Fe^{+++}$ or $Fe^{++}$ ions.

Metal binding compounds in the medium include any macromolecules which can interact with or bind with transition elements and facilitate their uptake by cells. Such interaction/binding can be covalent or non-covalent in nature. The metal-binding compound used in this aspect of the invention is preferably selected from the group consisting of a polyol, a hydroxypyridine derivative, 1,3,5-N,N',N''-tris(2,3-dihydroxybenzoyl)amino-methylbenzene, ethylenediamine-N,N'-tetramethylenephosphonic acid, trisuccin, an acidic saccharide (e.g., ferrous gluconate), a glycosaminoglycan, diethylenetriaminepentaacetic acid, nicotinic acid-N-oxide, 2-hydroxy-nicotinic acid, mono-, bis-, or tris-substituted 2,2'-bipyridine, a hydroxamate derivative (e.g. acetohydroxamic acid), an amino acid derivative, deferoxamine, ferrioxannine, iron basic porphine and derivatives thereof. DOTA-lysine, a texaphyrin, a sapphyrin, a polyaminocarboxylic acid, an .alpha.-hydroxycarboxylic acid, a polyethylenecarbamate, ethyl maltol, 3-hydroxy-2-pyridine, and IRC011. In one aspect, the metal-binding compound is a polyol such as sorbitol or dextran, and particularly sorbitol. In a related aspect, the metal-binding compound is a hydroxypyridine derivative, such as 2-hydroxypyridine-N-oxide, 3-hydroxy-4-pyrone, 3-hydroxypypyrid-2-one, 3-hydroxypyrid-2-one, 3-hydroxypyrid-4-one, 1-hydroxypyrid-2-one, 1,2-dimethyl-3-hydroxypyrid-4-one, 1-methyl-3-hydroxypyrid-2-one, 3-hydroxy-2(1H)-pyridinone, ethyl maltol or pyridoxal isonicotinyl hydrazone. The metal binding compounds of the present invention can also bind divalent cations such as $Ca^{++}$ and $Mg^{++}$.

The culture medium of the present invention may comprise one or more ingredients selected from the group consisting of adenine, ethanolamine, D-glucose, heparin, a buffering agent, hydrocortisone, insulin, linoleic acid, lipoic acid, phenol red, phosphoethanolamine, putrescine, sodium pyruvate, tri-iodothyronine, thymidine, L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, L-valine, N-acetyl-cysteine, biotin, choline chloride, D-$Ca^{++}$-pantothenate, folic acid, i-inositol, niacinamide, pyridoxine, riboflavin, thiamine, vitamin $B_{12}$, Pluronic F68, recombinant insulin, a calcium salt, $CuSO_4$, $FeSO_4$, $FeCl_3$, $Fe(NO_3)_3$, KCl, a magnesium salt, a manganese salt, sodium acetate, NaCl, $NaHCO_3$, $Na_2HPO_4$, $Na_2SO_4$, a selenium salt, a silicon salt, a molybdenum salt, a vanadium salt, a nickel salt, a tin salt, $ZnCl_2$, $ZnSO_4$ or other zinc salts, wherein each ingredient is added in an amount which supports in vitro cell culture.

In another aspect, the culture medium of the invention may optionally further comprise one or more supplements selected from the group consisting of one or more cytokines, soy peptone, one or more yeast peptides and one or more plant peptides (most preferably one or more of rice, aloe vera, soy, maize, wheat, pea, squash, spinach, carrot, potato, sweet potato, tapioca, avocado, barley, coconut and/or green bean, and/or one or more other plants), e.g., see international application no. PCT/US97/18255, published as WO 98/15614.

The culture medium of the present invention may also optionally include one or more buffering agents to maintain an optimal pH. Suitable buffering agents include, but are not limited to, N-[2-hydroxyethyl]-piperazine-N'[2-ethanesulfonic acid] (HEPES), MOPS, MES, phosphate, bicarbonate and other buffering agents suitable for use in cell culture applications. A suitable buffering agent is one that provides buffering capacity without substantial cytotoxicity to the cells cultured. The selection of suitable buffering agents is within the ambit of ordinary skill in the art of cell culture.

The above-described media components when admixed together in solution form a complete culture medium of the present invention. A complete medium is suitable for use in the culture of a variety of mammalian cells, as described in more detail herein. Based on the information obtained herein, and knowledge possessed by those of ordinary skill in the art, one of ordinary skill in the art can obtain operative media formulations without undue experimentation.

Initially and prior to adaptation for growth in a chemically defined serum-free medium, host cells may be grown in standard media well known to one of ordinary skill in the art. The media will usually contain all nutrients necessary for the growth and survival of the cells. Suitable media for culturing eukaryotic cells are, Roswell Park Memorial Institute (RPMI) medium 1640 (RPMI 1640), Minimal Essential Medium (MEM), and/or Dulbecco's Modified Eagle Medium (DMEM), DMEM/F12, and ExCell 325 medium, all of which may be supplemented with serum and/or growth factors as indicated by the particular cell line being cultured. Notably, however, the invention provides that the serum in the media is then removed from the culture to obtain host cells that can grow in serum-free medium. Thus, the invention provides optimal media for culturing host cells under serum-free conditions for maximal production of rFurin. In a further aspect, the cells are grown in serum-free medium in suspension culture. Recipes for the various media of the invention are provided in the Examples herein.

In one aspect, an antibiotic or other compound useful for selective growth of transformed cells is added as a supplement to the media. The compound to be used will be dictated by the selectable marker element present on the plasmid with which the host cell was transformed. Selectable markers that confer resistance to particular drugs that are ordinarily toxic to an animal cell can be used in the methods and compositions of the invention. For example, where the selectable marker element is kanamycin resistance, the compound added to the culture medium will be kanamycin. Other compounds for selective growth include ampicillin, tetracycline, geneticin, neomycin, zeomycin (zeo); puromycin (PAC); Blasticidin S (BlaS), and GPT. Additional selectable markers are known in the art and useful in the compositions and methods of the invention.

Metabolic enzymes that confer cell survival or induce cell death under prescribed conditions can also be used in the methods and compositions of the inventions. Examples include, but are not limited to: dihydrofolate reductase (DHFR); herpes simplex virus thymidine kinase (TK), hypoxanthine-guanine phosphoribosyltransferase (HGPRT), and adenine phosphoribosyltransferase (APRT), which are genes which can be employed in cells lacking TK, HGPRT or APRT, respectively. The worker of ordinary skill in the art will appreciate, however, that a rFurin product of the invention will be essentially free of these added proteins.

The medium can be used to culture any host cells or hosts known in the art for recombinant protein production. In one aspect of the invention, an exemplary host cell is a CHO cell. In a further aspect of the invention, the medium is used to culture CHO cells in suspension.

When the recombinant protein of interest is secreted into the medium by the host cells, the medium can be harvested periodically, so that the same host cells can be used through several harvest cycles. Culture medium may be added in a batch process, e.g. where culture medium is added once to the cells in a single batch, or in a fed batch process in which small batches of culture medium are periodically added. Medium can be harvested at the end of culture or several times during culture. Continuously perfused production processes are also known in the art, and involve continuous feeding of fresh medium into the culture, while the same volume is continuously withdrawn from the reactor. Perfused cultures generally achieve higher cell densities than batch cultures and can be maintained for weeks or months with repeated harvests. Thus, chemostat cultures and batch reefed cultures are both suitable for the manufacturing of rFurin, as are other culture methods known in the art.

A variety of culture systems are known in the art, including T-flasks, spinner and shaker flasks, roller bottles and stirred-tank bioreactors. Roller bottle cultivation is generally carried out by seeding cells into roller bottles that are partially filled (e.g., to 10-30% of capacity) with medium and slowly rotated, allowing cells to attach to the sides of the bottles and grow to confluency. The cell medium is harvested by decanting the supernatant, which is replaced with fresh medium. Anchorage-dependent cells can also be cultivated on microcarrier, e.g. polymeric spheres, that are maintained in suspension in stirred-tank bioreactors. Alternatively, cells can be grown in single-cell suspension.

The amount of rFurin produced by a host cell can be evaluated using standard methods known in the art. Such methods include, without limitation, Western blot analysis, SDS-polyacrylamide gel electrophoresis, non-denaturing gel electrophoresis, High Performance Liquid Chromatography (HPLC) separation, immunoprecipitation, ELISA, and/or activity assays such as DNA binding gel shift assays. The invention also contemplates that specific productivity (expressed as amount of protein/cell/day) of rFurin can be evaluated using standard methods as known in the art and as described herein.

"Substantially animal protein-free rFurin" is defined as encompassing preparations of rFurin comprising host cell protein in a concentration which ranges from between about 0.1 to 0.6 ng protein or less/Unit furin activity or between about 2 and 11 μg protein or less/mL and essentially lacking contaminating proteins from serum in the culture medium. In one aspect, the substantially animal protein-free rFurin encompasses preparations of rFurin comprising host cell DNA in a concentration which ranges from between about 0 to 0.4 pg DNA or less/Unit furin activity or between about 0 and 24 ng DNA or less/mL and essentially lacking contaminating proteins from serum in the culture medium. In one aspect, host cells expressing rFurin are grown in a chemically-defined, serum-free medium. Alternatively, the cells may be grown in medium with serum and purified according to methods provided herein.

Host cells expressing rFurin are cultured in suspension in a medium free of animal (including human) derived substances under chemostat conditions. The cells are removed by filtration and the rFurin containing cell culture supernatant is concentrated by ultrafiltration and purified by ion exchange chromatography to result in a solution of rFurin with an activity of at least about 1000 Units/ml, of at least about 2000 Units/ml, of at least about 3000 Units/ml, of at least about 4000 Units/ml, of at least about 5000 Units/ml, of at least about 6000 Units/ml, of at least about 7000 Units/ml, of at least about 8000 Units/ml, of at least about 9000 Units/ml, of at least about 10000 Units/ml, of at least about 15000 Units/ml, of at least about 20000 Units/ml, of at least about 25000 Units/ml, of at least about 30000 Units/ml, of at least about 35000 Units/ml, of at least about 40000 Units/ml, of at least about 45000 Units/ml, of at least about 50000 Units/ml, of at least about 55000 Units/ml, of at least about 60000 Units/ml, of at least about 65000 Units/ml, of at least about 70000 Units/ml, of at least about 75000 Units/ml, of at least about 80000 Units/ml, of at least about 85000 Units/ml, of at least about 90000 Units/ml, of at least about 95000 Units/ml, of at least about 100000 Units/ml, of at least about 120000 Units/ml, of at least about 140000 Units/ml, of at least about 160000 Units/ml, of at least about 180000 Units/ml, of at least about 200000 Units/ml, and of at least about 500000 Units/ml, and up to more than 500000 U/ml.

In another aspect the purified solution of recombinant furin of the invention has a specific activity of at least about 10 U/μg protein, at least about 20 U/μg protein, at least about 30 U/μg protein, at least about 40 U/μg protein, at least about 50 U/μg protein, at least about 60 U/μg protein, at least about 70 U/μg protein, at least about 80 U/μg protein, at least about 90 U/μg protein, at least about 100 U/μg protein, at least about 120 U/μg protein, at least about 140 U/μg protein, at least about 160 U/μg protein, at least about 180 U/μg protein, at least about 200 U/μg protein, at least about 250 U/μg protein, at least about 300 U/μg protein, at least about 350 U/μg protein, at least about 400 U/μg protein, at least about 450 U/μg protein, at least about 500 U/μg protein, at least about 550 U/μg protein, at least about 600 U/μg protein, at least about 650 U/μg protein, at least about 700 U/μg protein, at least about 750 U/μg protein, at least about 800 U/μg protein, at least about 850 U/μg protein, at least about 900 U/μg protein, at least about 950 U/μg protein, and at least about 1000 U/μg protein.

In another embodiment, the purified solution of rFurin in the invention contains host cell protein at a concentration of less than about 20.0 μg/ml, less than about 19.0 μg/ml, less than about 18.0 μg/ml, less than about 17.0 μg/ml, less than about 16.0 μg/ml, less than about 15.0 μg/ml, less than about 14.0 μg/ml, less than about 13.0 μg/ml, less than about 12.0 μg/ml, less than about 11.0 μg/ml, less than about 10.5 μg/ml, less than about 10.0 μg/ml, less than about 9.5 μg/ml, less than about 9.0 μg/ml, less than about 8.5 μg/ml, less than about 8.0 μg/ml, less than about 7.5 μg/ml, less than about 7.0 μg/ml, less than about 6.5 μg/ml, less than about 6.0 μg/ml, less than about 5.5 μg/ml, less than about 5.0 μg/ml, less than about 4.5 μg/ml, less than about 4.0 μg/ml, less than about 4.0 μg/ml, less than about 3.5 μg/ml, less than about 3.0 μg/ml, less than about 2.5 μg/ml, less than about 2.0 μg/ml, less than about 1.5 μg/ml, less than about 1.0 μg/ml, less than about 0.5 μg/ml, less than about 0.4 μg/ml, less than about 0.3 μg/ml, less than about 0.2 μg/ml, less than about 0.1 μg/ml, and about 0 μg/ml.

In another aspect, the purified solution of rFurin in the invention contains host cell protein at a concentration of less than about 1.0 ng protein/U rFurin, less than about 0.95 ng protein/U rFurin, less than about 0.90 ng protein/U rFurin, less than 0.85 ng protein/U rFurin, less than about 0.80 ng protein/U rFurin, less than about 0.75 ng protein/U rFurin, less than about 0.70 ng protein/U rFurin, less than about 0.65 ng protein/U rFurin, less than about 0.60 ng protein/U rFurin, less than about 0.55 ng protein/U rFurin, less than about 0.50 ng protein/U rFurin, less than about 0.45 ng protein/U rFurin, less than 0.40 ng protein/U rFurin, less than about 0.35 ng protein/U rFurin, less than about 0.30 ng protein/U rFurin, less than about 0.25 ng protein/U rFurin, less than about 0.20 ng protein/U rFurin, less than about 0.15 ng protein/U rFurin, less than about 0.10 ng protein/U rFurin, less than about 0.05 ng protein/U rFurin, less than about 0.04 ng protein/U rFurin, less than about 0.03 ng protein/U rFurin, less than about 0.02 ng protein/U rFurin, less than about 0.01 ng protein/U rFurin, and about 0 ng protein/U rFurin.

The examples herein below demonstrate the invention using CHO host cells to produce rFurin, however, the worker of ordinary skill will realize that any host cell type can be similarly adapted for producing the rFurin of the invention. CHO cells have been widely used in the production of recombinant proteins, and engineered CHO cells (those in which a CHO cell line is transfected with a product gene and a selectable marker gene) are routinely grown in culture medium containing serum. However, the use of serum poses a number of problems. Serum is an expensive commodity, which is not readily available in amounts required for commercial production. Serum is also a biochemically undefined material and contains many components which have not been fully identified nor their actions determined. Thus serum will differ from batch to batch, possibly requiring testing to determine levels of the various components and their effect on the cells.

In addition, serum is frequently contaminated with microorganisms such as viruses and mycoplasma many of which may be harmless, but still represent an additional unknown factor. Furthermore, the presence of animal proteins in culture media can require lengthy purification procedures. In particular, the presence of bovine antibodies in bovine serum albumin (BSA) makes purification of the desired antibodies expressed by the recombinant CHO cell line extremely difficult. Removal of bovine antibody from medium prior to use is possible, but this removal and the additional product testing required after removal adds greatly to the cost of production of the product. Consequently, there are benefits in using a culture medium devoid of animal components which will support cellular growth, especially of CHO cells. While CHO cells do not readily grow in serum-free conditions, the present invention provides rFurin grown in CHO cells under serum-free conditions.

Engineered CHO cells are also difficult to grow in suspension. It is highly desirable to achieve growth in suspension when using the cells to express a product like rFurin. For the production of such a biological protein on a commercial scale, it is desirable to be able to support growth in fermenters of a considerable size. A suitable medium is also required to support the cells so that they may grow in large production conditions. Such suitable media are set out in the Examples herein. The worker of ordinary skill in the art will appreciate that any methods of culturing cells in the art can be used in culturing the host cells comprising rFurin as set out in the invention. Non-limiting examples of culture methods are provided in the Examples herein.

The invention also provides purification methods that are carried out after cells are grown in serum-free medium to remove CHO cell proteins from rFurin. The worker of ordinary skill in the art will appreciate that any methods of protein purification known in the art can be used in the purification of rFurin from the culture medium. Non-limiting examples of purification methods are provided in the Examples herein. Accordingly, rFurin which is essentially substantially free from all animal source protein can be produced. The substantially animal protein-free rFurin is optionally stored frozen until use.

EXAMPLES

Additional aspects and details of the invention will be apparent from the following examples, which are intended to be illustrative rather than limiting. Example 1 describes the construction of a rFurin expression plasmid and host cell transfection; Example 2 describes the processes of adapting the rFurin-expressing CHO cell clones to growth in serum-free conditions; Example 3 describes a process of optimization for manufacturing rFurin in animal-protein free medium; Example 4 describes the purification of rFurin; Example 5 sets out the downstream processing (concentration and purification) and analysis of the large scale production of rFurin; and Example 6 demonstrates the safety, sterility, and stability testing that is performed to determine and maintain the quality of the host cell bank.

Example 1

Construction of a Recombinant Furin Expression Plasmid and Host Cell Transfection A detailed description of the furin progenitor plasmids used to construct a rFurin expression plasmid designated #556 is set out in Table 1. Expressed under control of a constitutive cytomegalovirus (CMV) promoter, the mature rFurin contains the catalytic domain, the P domain, and a small portion of the cystine-rich domain whereas regions located C-terminal to amino acid 577 are removed leading to a fully secreted active protease.

A description of the construction of the DHFR-vector used as the selection plasmid is depicted in Table 2. For the development of stably expressing CHO/rFurin cell clones designated #488-3 and #289-20, CHO cells lacking a functional endogenous DHFR gene were co-transfected with plasmids #556 and #73 employing calcium phosphate co-precipitation. Clones secreting high levels of rFurin were selected in several rounds of subcloning and amplification using the DHFR/MTX selection system.

TABLE 1

Description of furin plasmid generation

| Plasmid | Description | Comments |
|---------|-------------|----------|
| #177 | Original plasmid obtained from Wim J. M. van de Ven (University of Leuven, Belgium). A pUC18-based plasmid containing the 4.0 kbp EcoRI fragment of the human furin cDNA (2.385 kbp) with additional sequences of the 5'- and 3'-untranslated regions (UTR). | Carried out in the University of Leuven, Belgium. |
| #180 | Human full-length furin expression vector. | The 2.8 kbp SmaI/AvrII fragment of plasmid #177, comprising the complete furin cDNA (2.385 kbp) and in addition ~50 bp of the 5'-UTR and ~400 bp of the 3'-UTR, was cloned into the expression vector #55. |
| #55 | Eukaryotic expression plasmid from Clontech (Palo Alto, CA, USA) which has been modified to contain a multiple cloning site instead of the β-galactosidase cDNA. The plasmid provides a human cytomegalovirus immediate early (CMV IE) gene promoter and enhancer, the RNA splicing signals from the SV40 genome consisting of the late viral protein gene 16s/19s splice donor and acceptor sequences, and the SV40 polyadenylation signal. The original | The β-galactosidase NotI-cassette was removed and a multiple cloning site was inserted instead having amongst other restriction sites also the unique sites for SmaI and AvrII. |

TABLE 1-continued

Description of furin plasmid generation

| Plasmid | Description | Comments |
|---|---|---|
| | vector pCMVβ is a pUC19 derivative containing the *E. coli* ~3.4 kbp β-galactosidase cDNA inserted into the NotI site. | |
| # 229 | Human furin lacking the C-terminal sequences from position 578 to 794 spanning the cysteine-rich, the transmembrane and the cytoplasmic regions. After glycine 577, 4 additional glycines as 'spacer' and 10 histidine residues were introduced. | Between the SauI and AvrII sites, an appropriate reannealed oligodesoxynucleotide-linker was inserted coding for 4 glycines, 10 histidines followed by a stop codon. |
| # 378 | Derivative of plasmid # 229. Truncated furin after glycine 577 containing 10 histidines but without 4 glycines. | The 12 bps coding for 4 glycines located on a SauI/Hind III fragment were removed by PCR. The modified fragment was then religated into the plasmid-baekbone. |
| # 556 | Derivative of plasmid # 378. Truncated furin after glycine 577 which is devoid of any additional heterologous sequences. | Deletion of 30 bps coding for the 10 histidine residues by PCR. The modified SauI/Hind III fragment was relegated into the plasmid-backbone. |

TABLE 2

Description of DHFR plasmid generation

| Plasmid | Description | Comments |
|---|---|---|
| # 29 | The original plasmid named pAdD26SV(A)-3 was obtained from H. J. Hauser (GBF, Braunschweig, Germany). This plasmid contains the full length murine dihydrofolate reductase (DHFR) cDNA behind an adenovirus major late promoter. | Constructed outside Baxter. |
| # 73 | Murine DHFR-cDNA under control of the SV40 early promoter. | The PstI fragment comprising the DHFR cDNA and the SV40 polyadenylation signal of plasmid # 29 was cloned into the PstI site of plasmid # 53. Due to the cloning strategy, plasmid # 73 contains two polyadenylation signals. |
| # 53 | Eukaryotic expression vector from Clontech (Palo Alto, CA, USA) which has been modified to contain a multiple cloning site instead of the β-galactosidase cDNA. The plasmid provides a simian virus 40 (SV40) early gene promoter and enhancer, the RNA splicing signals from the SV40 genome consisting of the late viral protein gene 16s/19s splice donor and acceptor sequences, and the SV40 polyadenylation signal. The original vector pSV40β is a pUC19 derivative containing the *E. coli* ~3.4 kbp β-galactosidase cDNA inserted into the NotI site. | The β-galactosidase NotI-cassette was removed and a multiple cloning site was inserted instead having amongst other restriction sites also a unique site for PstI. |

Transfected CHO cells were grown in DHFR-medium, composed of DMEM NUT MIX F12 (1:1) without hypoxanthine, thymidine and glycine supplemented with Hepes, L-glutamine, Penicillin-Streptomycin, and with 5% or 10% dialyzed, gamma-irradiated FBS (=5% DHFR, 10% DHFR). Dialyzed and gamma-irradiated FBS was purchased from Life Technologies with full documentation of certificates of analysis, origin and irradiation. The preparation of gamma-Trypsin solution (1 mg/ml) was performed at Baxter in Orth, Austria, by the department of Media Preparation/PCC.

Figure 2:
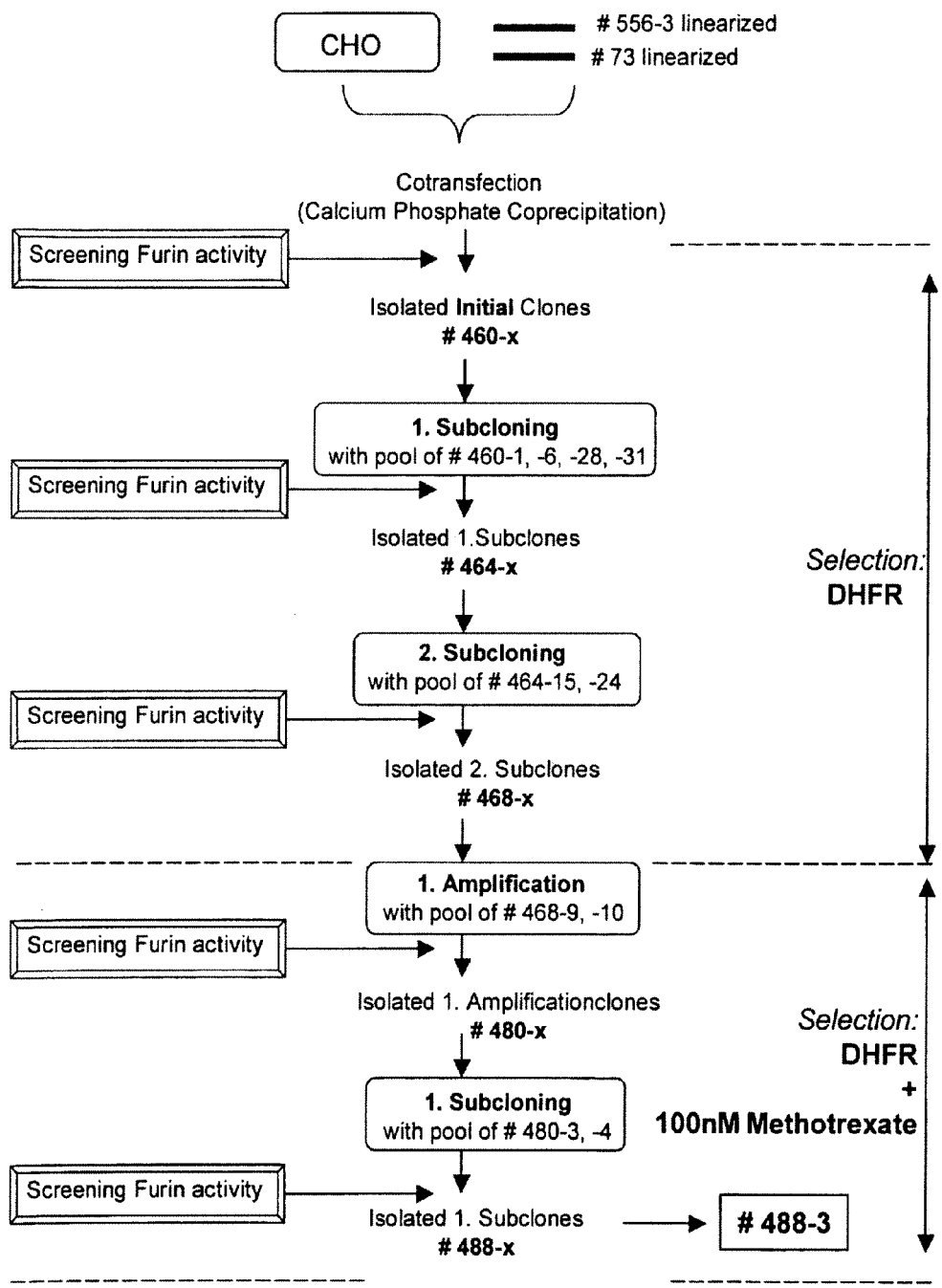
FIG. 2 depicts a pedigree of the generation of the CHO/rFurin clone #488-3.

A pedigree of the generation of the CHO/rFurin clone #488-3 is depicted in FIG. 2. Clone CHO/rFurin #488-3 was obtained from initial clones which underwent two rounds of subcloning in 10% DHFR selection medium before entering amplification in selection medium supplemented with 100 nM MTX in which one round of subcloning in medium containing unchanged MTX concentration was performed. Clone #448-3 was expanded for freezing. The CHO/rFurin clone #289-20 was likewise prepared and expanded. However, clone #289-20 is a successor clone derived from clone

Figure 3:
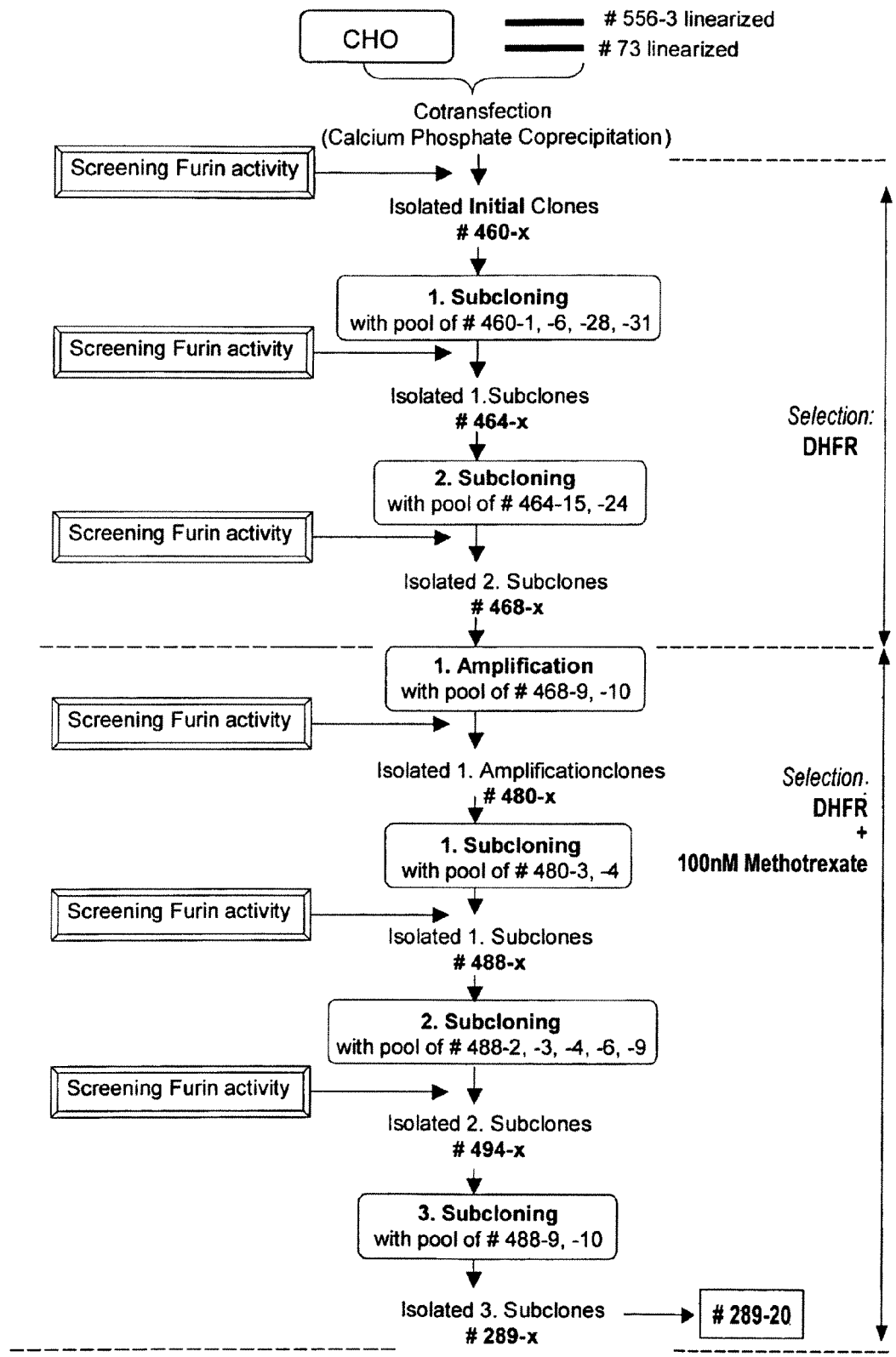
FIG. 3 shows a pedigree of the generation of the CHO/rFurin clone #289-20.

488-3. A pedigree of the generation of the CHO/rFurin clone #289-20 is depicted in FIG. 3.

Furin activity was measured in the conditioned medium of clones, which were cultured for 24 hrs in serum-free DHFR medium. Cell clones which showed high furin activity (U/$10^6$ cells per 24 hrs) were selected. Selected high producer clones were expanded for the preparation of freeze stock ampules, and used for splitting for the next cloning round. Isolation and identification of high producer cell clones was performed. Cell densities were analyzed using the Casy cell-counter. Furin expression levels of up to 200-300 U/$10^6$ cells per 24 hrs were achieved for clone #488-3. Furin expression levels of up to 400 U/$10^6$ cells per 24 hrs were achieved for clone #289-20.

Example 2

Adapting the Recombinant Furin Expressing Cell Clones to Growth in Serum-Free Conditions The strategy for cell line adaptation and selection is to adapt the cell line to a serum- and protein-free cell line in either gradually in a step-wise dilution or abruptly. The purpose of this study was to find a CHO cell population growing under serum-free conditions, which was stably producing rFurin. The CHO cell clone #488-3 was used as starting material. The rFurin expressing cell clone CHO #488-3 was changed over to serum-free conditions in three parallel conducted adaptations as set out in detail below.

The serum depletion process started in spinner flasks with use of microcarriers to find a means to hold back cells in the phase of adaptation, since in that phase cells usually show slow growth. By using this method, it was possible to avoided, during subsequent media changes, diluting the cells to such concentrations where growth could be inhibited.

Three variants of an in-house developed medium, BAP, BAS, and BCS, (as shown in Table 3) were used during the course of this study.

TABLE 3

In-house media formulations of BAP, BAS and BCS

| Components | JDE Item No. | Concentration [g/kg] | BAP | BAS | BCS |
|---|---|---|---|---|---|
| DMEM/F12 | 0200437 | 11.745 | X | X | X |
| L-Glutamine | 0200444 | 0.600 | X | X | X[1] |
| Phenol red sodium salt | 0200425 | 0.008 | X | X | X |
| Putrescine dihydrochloride | 0200233 | 0.0036 | — | — | X |
| Iron (II) sulfate heptahydrate | 0200231 | 0.0006 | — | — | X |
| Ethanolamine | 0200426 | 0.00153 | X | X | X |
| Synperonic F68 | 0200172 | 0.250 | X | X | X[2] |
| Soy peptone | 0200171 | 2.50 | X | — | — |
| Sodium bicarbonate | 0301012 | 2.00 | X | X | X |
| WFI (water for injection) | F124 | ad 1 kg | X | X | X |

[1] Concentration of L-Glutamine in BCS: 0.900 g/kg
[2] Concentration of Synperonic F68 in BCS: 1.00 g/kg Depending on the purpose of the respective experiment these media variants were provided with different supplements, as listed in Table 4.

TABLE 4

Media and their supplements

| | Put[1] (mg/l) | Glut[2] (mg/l) | Synp[3] (mg/l) | Fe[4] (mg/l) | Zn[5] (mg/l) |
|---|---|---|---|---|---|
| ExCell 325PF CHO | — | 600 | — | — | 1.0 or 5.0 |
| BAS | 3.6 | 300 | 750 | 0.6 | 5.0 |
| BCS | — | — | — | — | 1.0 or 5.0 |

[1] Putrescine dihydrochloride
[2] L-Glutamine
[3] Synperonic F68
[4] Iron(II) sulfate heptahydrate
[5] Zinc(II) sulfate heptahydrate The following tables give an overview of media and reagents, which were used in the course of this study. Table 5 summarizes media and reagents which were used for the establishment of the pre-master cell bank clones PMCB#01 and the PMCB#04.

TABLE 5

Media and Reagents Used for the Establishment of PMCB#01 and PMCB#04

| | Description | Lot Number |
|---|---|---|
| MEDIA | 10% DHFR medium | #061005/09 |
| | BAP + 5% FBS | M/MAB-05/009, M/MAB-05/013 |
| | BAS + Put + Glut + Synp + Fe + 5% FBS | M/MAB-06/019 [4] |
| | BAS + Put + Glut + Synp + Fe | M/MAB-06/012 [1], M/MAB-06/017, M/MAB-06/031, M/MAB-06/036, M/MAB-06/044, M/MAB-06/048 [4], M/MAB-06/058 [4], M/MAB-06/061 [4] |
| | BAS + Put + Glut + Synp + Fe + Zn | M/MAB-06/063, M/MAB-06/069, M/MAB-06/072, M/MAB-06/074 [4], M/MAB-06/076 [4], M/MAB-06/079 [4] |
| | BCS + Zn | M/CLD-06/001 |
| REAGENTS | Gamma-Trypsin Solution 1 mg/ml | GT_04002_1 |
| | N1 Buffer pH 7.3 | N1_05001_2 |
| | Dimethylsulfoxide (Baxter Mat.No.: 33000000001/JDE 0200407) | 219102 |

TABLE 5-continued

Media and Reagents Used for the Establishment of PMCB#01 and PMCB#04

| Description | Lot Number |
|---|---|
| Cytopore 2 Carrier | Cyt2__24__06__001 [1] |
| Na$_2$HCO$_3$ - Solution | R/CBL/05/005 [1] |

[1] only applied to PMCB#01
[4] only applied to PMCB#04

Table 6 summarizes media and reagents which were used in the course of sub-cloning and establishing of thecorresponding evaluation cell banks (ECBs) of the sub-clones #488-3/CJ06-19/5F10 (5F10) and #488-3/CJ06-19/1E8 (1E8).

TABLE 6

Lot numbers of media and reagents used for the establishment of subclones 5F10 and 1E8

| | Description | Lot Number |
|---|---|---|
| MEDIA | 10% DHFR Anzuchtmedium | #061005/09 |
| | BAP + 5% FBS | M/MAB-05/009, M/MAB-05/013 |
| | ExCell + 5% FBS + Glut | M/MAB-05/017 |
| | ExCell + Glut | M/MAB-05/016, M/MAB-05/022, M/MAB-06/025, M/MAB-06/035, M/MAB-06/054, M/MAB-06/057, M/MAB-06/060 |
| | ExCell + Glut + Zn | M/MAB-06/067, M/MAB-06/071, M/MAB-06/104, M/MAB-06/142 |
| | ExCell + Glut/BAS + Put + Glut + Synp + Fe (1:1) | M/MAB-06/062 |
| | ExCell + Glut/BAS + Put + Glut + Synp + Fe + Zn (1:1) | M/MAB-06/070 |
| | ExCell + Glut/BCS (1:1) | M/MAB-06/077 |
| | ExCell + BCS + Glut + Zn | M/MAB-06/090, M/MAB-06/103, M/MAB-06/106 |
| | BCS + Zn | M/MAB-06/105, M/MAB-06/110, M/MAB-06/116, M/MAB-06/143, M/MAB-06/129, M/MAB-06/149 |
| REAGENTS | Gamma-Trypsin Solution 1 mg/ml | GT__04002__1 |
| | Trypsin-Inhibitor Solution 1 mg/ml | TI__04001__1 |
| | N1 Buffer pH 7.3 | N1__05001__2 |
| | Dimethylsulfoxid (Baxter Mat.No.: 33000000001/JDE 0200407) | 219102 |
| | Na$_2$HCO$_3$ - Solution | R/CBL/05005 |

The lot numbers of all supplements, which were added to the media, are referenced in the appropriate manufacturing protocol of the corresponding medium. Other media additives are listed in Table 7.

TABLE 7

Other Media Additives

| Description | Manufacturer | Catalog No. | Lot No. | Provided by |
|---|---|---|---|---|
| Aqua Bidest | Fresenius | 8230673 | SBV 093 | Manufacturer |
| Aqua Bidest | Fresenius | B230673 | TDV 252 | Manufacturer |
| Aqua Bidest | Fresenius | B230673 | TKV 261 | Manufacturer |
| Aqua Bidest | Fresenius | B230673 | UCV 282 | Manufacturer |
| Cytopore 2 Carrier | Pharmacia Biotech | 17-1271-03 | 249933 | Pilot Plant II |
| DMEM NUT MIX F12 [2] | Gibco | 041-90163M | 3097428 | Recombinant Cell Lines |
| ExCell 325PF CHO | JRH | 14340 | 4N0597 | Manufacturer |
| ExCell 325PF CHO | JRH | 14340 | 5L0191 | Manufacturer |
| ExCell 325PF CHO | SAFC Biosciences | 14340C | 5M0775 | Manufacturer |
| FBS [1, 2] | Gibco | 10603-017 | 3092829A | Recombinant Cell Lines |
| FBS [1] | JRH | 12303 | 1A0348 | Manufacturer |
| Glutamin [2] | Gibco | 25030-024 | 3096452 | Recombinant Cell Lines |
| Glutamine | Sigma | G-5763 | 117 H 00655 | Manufacturer |
| Hepes-Puffer [2] | Gibco | 15630-056 | 3094125 | Recombinant Cell Lines |
| Paraformaldehyde | Sigma | P-6148 | 043 K 0653 | Manufacturer |
| Paraforrnaldehyde | Sigma | P-6148 | 045 K 0703 | Manufacturer |
| Paraformaldehyde | Sigma | P-6148 | 118 H 0987 | Manufacturer |
| Penic./Streptomycin [2] | Gibco | 15140-122 | 1276184 | Recombinant Cell Lines |

TABLE 7-continued

Other Media Additives

| Description | Manufacturer | Catalog No. | Lot No. | Provided by |
|---|---|---|---|---|
| Putrescine | Sigma | P5780 | 22 K 2615 | Manufacturer |
| Synperonic F68 | Serva | 35724 | 01137 | Manufacturer |

[1] animal derived materials: for certificates refer to appendix
[2] ingredients of "10% DHFR medium", only used in the beginning of experiment SF05-80

Adaptation to serum-free conditions was performed in T-flasks or in spinner flasks in conjunction with cell retention (centrifugation and the like) by weaning off the cells from fetal bovine serum (FBS).

Suspension cultures in T-flasks were incubated at 36±2° C. and 7.5±1.0% $CO_2$. The culture in spinner flasks was performed in Techne and Bellco spinners without carriers operating at 36±2° C. with 80 rpm and 130 rpm, respectively.

The subcloning of the CHO/rFurin cell clone #488-3, subsequent to its adaptation to serum-free medium conditions, resulted in a CHO cell clone, growing in suspension in serum-free in-house medium, stably producing rFurin in a large amount. The procedure was based on the limited dilution method. Briefly, the cell suspension was diluted so that 100 μl of the suspension contains a cell. The wells of a 96-well plate were filled with 100 μl of this suspension. In theory, each well contains one cell for clonal development. As these single cells start to grow, clones develop. Thus, every newly generated cell can be traced back to the first original cell in the well. The clones were expanded in 24-well plates, then in T25 flasks, then in T75 flasks, and then in T175 flasks.

During culture, in process controls (IPC) were performed to monitor growth conditions and to measure rFurin expression. Cell densities during culture were measured using the Casy instrument. The Nucleo counter instrument was applied for the detection of cell nuclei after CTX extraction. Determination of cell density and viability after thawing was performed with trypan blue exclusion method using a hemacytometer. Cell density and viability was also analyzed by using an automated trypan blue exclusion method performed by the Cedex instrument.

The supernatants of the cell cultures were used to determine the amount and activity of expressed rFurin. Fluorescence activated cell sorting (FACS) analysis was used to see the ratio of producer to non-producer cells in a given cell population. Morphology and growth behavior of cells were determined by optical control. Additionally, the supernatant of the cell cultures was also examined to monitor medium conditions, such as the determination of the pH value and the residual concentration of glucose, glutamine, lactate, and ammonium. These analyses were performed by means of a NOVA instrument.

In the course of this study, two pre-master cell banks (PM-CBs) PMCB#01 and PMCB#04 were produced and two cell clone lines were established as set out below. Evaluation cell banks (ECB) (see Table 15) were also generated.

Preparation and QC Testing of PMCB#01

One vial of the CHO/rFurin #488-3 (ECB#01) was thawed in BAS medium containing additives (Put, Glut, Synp and Fe) and 5% FBS. The cells were cultured cells for five days in a T175. The cells were then adapted to serum-free conditions as set out below.

Cells were prepared in 150 ml growth medium (BAS with Put, Glut, Synp and Fe) containing 5% FBS, 0.2 g/l. Cytopore 2 carriers were used for the adaptation to serum-free conditions. Having inoculated the 5-day old cell suspension resulting in a starting cell density of about $2.0 \times 10^5$ cells/ml, the cells attached to the porous carriers within the first hours. Thus, the cells were kept in the spinner flask, while the growth medium was exchanged to reduce the serum concentration in two steps, from 5% to 3.8% to 0% on day 05. During the following culture period the cells got adapted to the serum-free medium conditions. The cells detached from the surface of the carriers and continued their growth in suspension. The cell density and the viability of the suspension cells increased continuously. Every two to three days the suspension cells were split in a ratio of 1:2.

An evaluation cell bank (ECB) was then prepared. On culture day 28, cells having a viability of greater than 60% were transferred to a new experiment. The culture was grown in 200-300 ml BAS medium (with Put, Glut, Synp and Fe) in a Bellco spinner without carriers. According to the determined CASY cell density, the suspension culture was split every two to three days to a starting cell density of about $2.0 \times 10^5$ cells/ml. After 16 days, when the cell culture reached a viability of greater than 80%, the evaluation cell bank (ECB) consisting of six vials of cells was produced.

One vial of the ECB was thawed in a new experiment. The cells were grown for four days in a T175 in BAS medium with Put, Glut, Synp, Fe and Zn. Cells were then transferred to a Bellco spinner containing up to 600 ml BAS medium with Put, Glut, Synp, Fe and Zn. Again, every two to three days the suspension culture was split to a starting cell density of about $2.0 \times 10^5$ cells/ml. On culture day 13, 143 ml of the cell suspension were removed for the preparation of the PMCB#01, consisting of 20 vials. The cells were expanded and quality control tests were performed on PMCB#01.

Preparation and QC Testing of PMCB#04

One vial of the CHO/rFurin #488-3 (ECB#01) was thawed in BAS medium containing Put, Glut, Synp, Fe and 5% FBS. Half of the six day old culture was transferred to a new experiment for adaptation to serum-free conditions.

Here, the adaptation to serum-free conditions was not performed step by step, but rather was carried out abruptly. A Bellco spinner flask was prepared with BAS medium (with addition of Put, Glut, Synp and Fe) containing no FBS and no carriers. The cells were inoculated with a starting cell density of about $2.5 \times 10^5$ cells/ml. Due to the sudden serum-free conditions, the doubling time of the cells decreased to a rather low level. To avoid diluting the cells to such a concentration where growth could be possibly inhibited, the medium was changed by spinning down the cell suspension. The cell pellet was resuspended in fresh growth medium. Culture splits were performed when the cell density was greater than $4.0 \times 10^5$ cells/ml. After having reached a minimum viability of about 50% at culture day 15, the cells started to recover and, from culture day 32 and on, their viability increased to between 85-90%. On culture day 61, the adapted cells were frozen as an ECB consisting of 15 vials.

One vial of the ECB was thawed in a new experiment in serum-free BAS medium comprising Put, Glut, Synp and Fe. After the culture was cultured in T175 flasks for seven days, it was transferred to a Bellco Spinner, where the cells grew for two further days. Then, the addition of Zn was tested. About 100 ml of the centrifuged cell suspension were resuspended in serum-free BAS medium containing Put, Glut, Synp, Fe and Zn. The suspension was cultured in a Bellco Spinner. According to the determined CASY cell density, every two to three days the suspension culture was split to a starting cell density of about $2.0 \times 10^5$ cells/ml.

For inoculum preparation and to be able to produce a large amount of a homogenous cell suspension for the generation of the PMCB#04, the cell culture was scaled up to 1000 ml in a Bellco Spinner. On culture day 02, 465 ml of the cell suspension were used to produce the PMCB#04, consisting of 20 ampules. The cells were expanded and quality control tests were performed on PMCB#04.

Figures 4A, 4B:
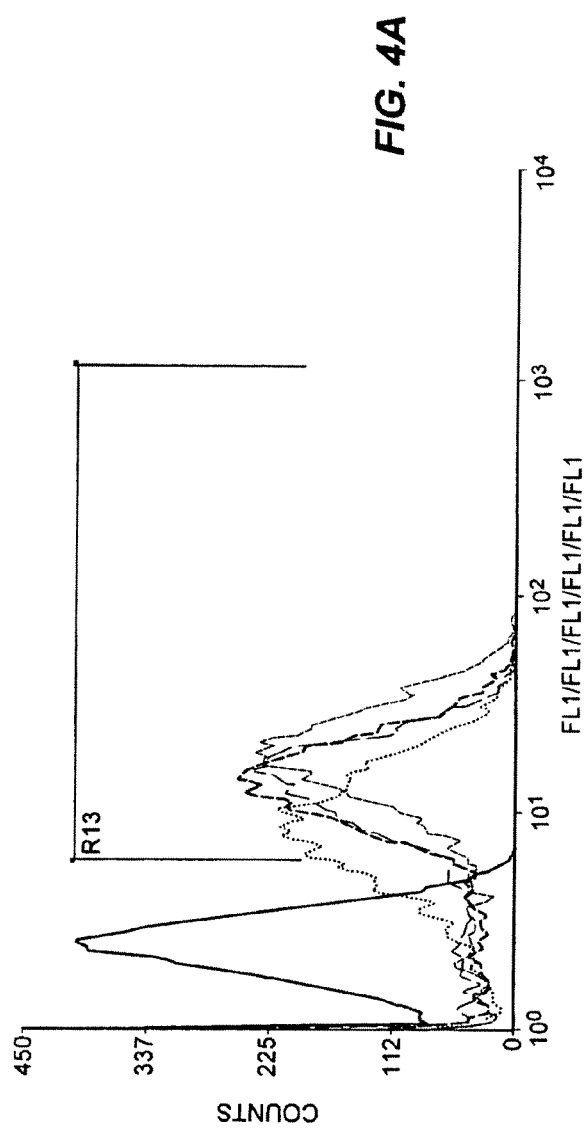
FIG. 4 sets out a comparison of the graphical distribution of the rFurin producers in the cell populations of PMCB#01 and PMCB#04. 80.74% of the cells in PMCB#04 express rFurin; 74.06% of the cells in PMCB#01 express rFurin.

FIG. 4 sets out a comparison of the graphical distribution of the rFurin producers in the cell populations of PMCB#01 and PMCB#04. 80.74% of the cells in PMCB#04 express rFurin. 74.06% of the cells in PMCB#01 express rFurin.

CHO/rFurin #488-3 subclones CJ06-19/5F10 and CJ06-19/1E8 were then generated. An ampule of the CHO/rFurin clone #488-3 was thawed and the culture was passaged in a T175 flask. On culture day 17, three different media were tested, BAP medium (developed by Baxter), CD-CHO (provided by Gibco) and ExCell 325PF CHO (provided by JRH), each of them contained 5% FBS. After four days of growth in T175 flasks, cells grown in ExCell medium were adapted to serum-free conditions.

The cells were weaned off from serum in small steps. The whole procedure ranged over three experiments. First, the anchorage-dependent cells were initially cultured in T175 flasks in ExCell 325PF CHO containing 5% FBS. The serum was then slowly reduced to 0.5% on culture day 13. During the next 13 culture days two splits were performed, wherein the serum concentration was further reduced to 0.25% and the viability decreased to lesser than 70%. The cells lost their anchorage-dependent behavior, showed more and more spherical shape, and started to grow in suspension.

The last step of serum reduction occurred in a Techne Spinner in ExCell 325PF CHO medium containing 0.25% FBS and no carriers. After a culture period of 23 days, the serum concentration reached 0%. Cells were split and cultured to keep all relevant parameters in their given range. The cell density moved between 0.15 to $0.9 \times 10^6$ cells/ml. The viability dropped to less than 40% during the first week, but then returned to values of greater than 90%. On culture day 42, the adapted cells were frozen in the ECB/CJ06-20 consisting of 20 vials.

The cells were then subcloned. A cell suspension was diluted with preconditioned ExCell 325PF CHO in such a way, that 100 µl of the suspension theoretically contained 0.5-1.0 cells. In the subcloning experiment, five 96-well plates were filled with 100 µl of this cell suspension per well. The day after the seeding of the cells, the wells were searched for single cells under the microscope. Wells containing one cell were marked and observed further. Addition and exchange of preconditioned ExCell 325PF CHO were performed when necessary. When the cell died or in the absence of cell division during the next two weeks, the relevant well was excluded from the experiment.

Two single cells showed growth. The evolved clones, having reached an appropriate size, were transferred into a well of a 24-well plate. Here, the exchange of preconditioned ExCell 325PF CHO was also performed according to the growth and the requirements of the culture. The subclones CJ06-19/5F10 and CJ06-19/1E8 were transferred into a T25 flask on culture day 07 and day 10, respectively.

The ECBs were prepared in ExCell medium. These ECBs present the source material for further investigations concerning the two subclones, such as a re-adaptation from expensively purchased media to a more economical formulation, self-developed by Baxter. ECB of sub clone CJ06-19/5F10, CJ06-42, was expanded in ExCell 325PF CHO medium from a T25, to a T75, to a T175, and then into a Bellco Spinner. The ECB/CJ06-63 consisting of 10 vials were frozen from a culture out of the T175 on day 21. ECB of subclone CJ06-19/1E8, CJ06-43, was also expanded in ExCell 325PF CHO medium. The culture was expanded from a T25, to a T75, to a T175, and then into a Bellco Spinner. The ECB/CJ06-64 consisting of 10 vials were frozen from a culture out of the T175 on day 18.

The ECBs (Subclones 5F10 and 1E8) were adapted to BCS medium as set out below. The subclone CJ06-19/5F10 of ECB clone CJ06-19 was thawed in experiment CJ06-66, and then by adding BCS medium to ExCell medium in an increasing volume, the cells were weaned from ExCell medium and acquired the ability to grow in BCS medium. The subclone CJ06-19/1E8 of ECB clone CJ06-19 was simultaneously adapted to BCS medium in a similar manner.

Table 8 shows all serum-free cell banks which were prepared in the course of this study.

TABLE 8

Summary of serum-free cell banks of rFurin expressing CHO cell clone #488-3

|  | Test No.: | Date | Name | Cell density/Amp | Amp. | Medium | Thawing contr. |
|---|---|---|---|---|---|---|---|
| PMCB#01 | DE06-02 | 10 Mar. 2006 | ECB/DE06-02 | $1.0 \times 10^7$ | 6 | BAS + Put + Glut + Synp + Fe | ok |
|  | CJ06-73 | 12 May 2006 | PMCB#01 | $1.5 \times 10^7$ | 20 | BAS + Put + Glut + Synp + Fe + Zn | ok |
| PMCB#04 | CJ06-51 | 11 Apr. 2006 | ECB/CJ06-51 | $1.2 \times 10^7$ | 15 | BAS + Put + Glut + Synp + Fe | ok |
|  | SK06-65 | 12 May 2006 | PMCB #04 | $1.5 \times 10^7$ | 20 | BAS + Put +Glut + Synp + Fe + Zn | ok |
| Sub Clones | CJ06-20 | 27 Feb. 2006 | ECB/CJ06-20 | $1.1 \times 10^7$ | 20 | ExCell + Glut | n.d. |
|  | CJ06-63 | 14 Apr. 2006 | Klon:CJ06-19/5F10 ECB/CJ06-63 | $1.0 \times 10^7$ | 10 | ExCell + Glut | ok |
|  | SK06-58 | 10 May 2006 | Klon:CJ06-19/5F10 ECB/SK06-58 | $1.0 \times 10^7$ | 5 | ExCell + Glut/ BAS + Put + Glut + Synp + Fe (1:1) | ok |
|  | SK06-83 | 19 Jun. 2006 | ECB/SK06-83 | $1.5 \times 10^7$ | 15 | ExCell + Glut/ BAS + Put + Glut + Synp + Fe + Zn (1:1) | ok |
|  | SK06-151 | 03 Nov. 2006 | Klon:CJ06-19/5F10 ECB/SK06-151 | $1.0 \times 10^7$ | 5 | BCS + Zn | n.d. |
|  | CJ06-64 | 14 Apr. 2006 | Klon:CJ06-19/1E8 ECB/CJ06-64 | $1.0 \times 10^7$ | 10 | ExCell + Glut | ok |

TABLE 8-continued

Summary of serum-free cell banks of rFurin expressing CHO cell clone #488-3

| Test No.: | Date | Name | Cell density/Amp | Amp. | Medium | Thawing contr. |
|---|---|---|---|---|---|---|
| SK06-59 | 10 May 2006 | Klon:CJ06-19/1E8 ECB/SK06-59 | $1.0 \times 10^7$ | 5 | ExCell + Glut/ BAS + Put + Glut + Synp + Fe (1:1) | ok |
| SK06-84 | 19 Jun. 2006 | ECB/SK06-84 | $1.5 \times 10^7$ | 15 | ExCell + Glut/BCS (1:1) | ok |
| SK06-152 | 03 Nov. 2006 | Klon:CJ06-19/1E8 ECB/SK06-152 | $1.0 \times 10^7$ | 7 | BCS + Zn | n.d. |

A comparison of PMCB#01 and PMCB#04 and subclones 5F10 and 1E8 is set out in Table 9.

TABLE 9

Comparison of PMCB#01, PMCB#04 and Subclones 5F10 and 1E8

| Cell population | Experiments | Evaluated period | Average values of | | | | | | | |
|---|---|---|---|---|---|---|---|---|---|---|
| | | | Cell density x [x$10^6$ cells/ml] | Viability [%] | Furin act. [U/ml] | FACS [%] | $\mu$ ($d^{-1}$) | g [h] | $q_p$ [U/($10^6$*d)] | $Q_p$ [U/(ml*d)] |
| PMCB#01 | CJ06-69 | 29 April-17 May 2006 | 1.16 | 84.4 | 274.87 | 71.30 | 0.494 | 35.94 | 123.0 | 77.1 |
| PMCB#04 | SK06-49, SK06-63 | 26 April-17 May 2006 | 1.10 | 94.4 | 287.03 | 72.02 | 0.614 | 28.52 | 207.7 | 96.8 |
| Clone 5F10 | CJ06-66, SK06-52 | 21 April-17 May 2006 | 0.59 | 94.3 | 105.57 | 83.30 | 0.523 | 37.43 | 135.0 | 40.8 |
| Clone 1E8 | CJ06-67, SK06-53 | 21 April-17 May 2006 | 0.59 | 94.8 | 95.55 | 88.34 | 0.512 | 39.01 | 114.4 | 35.7 |

The cell populations cultured in the experiments CJ06-69 as well as SK06-49 and SK06-63 represent the precursor cultures of the cell lines for the PMCBs. These cells were grown in BAS medium (with the addition of Put, Glut, Synp, Fe and Zn), and were frozen as PMCB#01 and PMCB#04, respectively.

The subclones 5F10 and 1E8 were grown in the commercially available medium ExCell 325PF CHO provided by JRH. Because the ability of growing in medium based on the BAS formulation was preferred, PMCB#01 and PMCB#04 were chosen for further production of rFurin.

As presented in Table 10, the cells of PMCB#04 showed better growth behavior in comparison to PMCB#01. Viabilities and growth rates were greater in PMCB#04, and generation doubling times were lower. The cell-specific as well as the volumetric production ratio of rFurin was also greater throughout the evaluated period of time. In a further experiment, the data concerning the viabilities was confirmed. One ampule of each of the PMCBs was thawed into a T175 flask containing BCS medium with Zn as additive. As shown in Table 10 the viability of PMCB#04 was again greater than that of PMCB#01.

TABLE 10

Thawing experiments of PMCB#01 and PMCB#04

| Cell population | experiment | cell density [x$10^7$ cells/vial] | viability [%] |
|---|---|---|---|
| PMCB#01 | CJ06-77 [75] | 1.05 | 68.7 |
| PMCB#04 | SK06-67 [76] | 0.99 | 77.4 |

Thus, PMCB#04 was chosen as the source material for the future production of a rFurin Master Cell Bank (MCB) and all further working cell banks (WCBs). The PMCB#04 consisting of 20 vials was established in compliance with the current Good Tissue Practice regulations. Quality Control (QC) testing was performed in accordance to requests of the ICH-Guideline Q5D. PMCB#04 was chosen for producing rFurin in manufacturing processes.

The growth medium is free of human or animal derived substances and is self-developed. Having the cells removed by filtration, the rFurin containing supernatant is concentrated by ultrafiltration. After purification by exchange chromatography, the activity of the rFurin solution is aimed to be at least 200 Units rFurin/ml.

Testing for mycoplasma, viruses, extraneous agents, sterility, and expression efficiency was carried out. The criteria for selection are high Furin activity (e.g., Furin protein, ELISA) and homogeneity of the cell population in immunoflourescence (FACS), performed on different subclones in comparison to initial clones #488-3 and #289-20, respectively. In addition, the impurity profiles have to be compared qualitatively (e.g. by UV-peak patterns after RP HPLC or by SDS-PAGE/Coomassie techniques).

Example 3

Optimization for Manufacturing Recombinant Furin in Animal Protein-Free Medium

This example describes the development and optimization process for the culture of the rFurin expressing CHO clone #488-3. Specific medium optimization with regard to amino acids, glucose, and NaHCO3 concentration was carried out, which resulted in increased cell growth rates and, higher productivities of the fermentation process. Optimization for inline controlled process parameters was carried out with the optimized medium formulation for pO2 (10%, 20% and 50%), and a factorial experiment was carried out to determine optimum pH (range 7.1-7.3) and temperature (range 35.1° C.-37.9° C.), which resulted in a significant yield improvement for CHO clone #488-3 when fermentation was carried out at lower temperatures between 35°-36° C.

As possible production modes, chemostat cultures and batch reefed cultures were compared, indicating that both process types are suitable for the manufacturing of rFurin, and give comparable yields with identical parameter settings. Specific experiments were carried out to investigate the influence of agitation types and rates in different bioreactor setups. It was shown that the specific growth rates and expression rates, cell densities and therefore volumetric productivities are strongly influenced by variations in the bioreactor setup, and that under conditions of increased agitation rates the yields could be significantly increased. Altogether, the influence of the main parameters of the rFurin upstream process are well characterized with regard to their effect, and a high yielding process could be transferred to the pilot plant for preclinical and clinical manufacturing. The details are set out below.

A subclone #488-03 was developed in-house which was adapted to a serum- and insulin-free medium. The following experiments were carried out in a FBS-free and insulin-free medium (BACD-medium) as the basic medium formulation (see Table 11).

TABLE 11

Components of the basic medium (BACD-medium)

| Component | Concentration [g/kg] |
|---|---|
| DMEM/F12 (1:1) | 11.76 |
| L-Glutamine | 0.6 |
| Ethanolamine | 0.00153 |
| Synperonic | 0.25 |
| Putrescine•2HCl | 0.0036 |
| FeSO4•7H2O | 0.0006 |
| CuSO4•5H2O | 0.00000125 |
| NaHCO3 | 2.0 |

In order to improve cell growth and to provide optimal conditions for cell propagation, an amino acid analysis of the supernatant of a chemostat culture was performed (see Table 12). As a result, three essential amino acids were added to the medium, namely methionine (10 mg/L), leucine (40 mg/L) and phenylalanine (10 mg/L). Fermentation was performed in a 1.5 L bioreactor at 37° C., pH 7.15 and a pO$_2$ of 20%.

TABLE 12

Amino acid analysis by HPLC

| Amino acids | BACD_24_06_014_026 Peak area [%] | FUR_06/10_M04_K06 relative peak area [%] | FUR_06/10_M04_K07 relative peak area [%] |
|---|---|---|---|
| Aspartic acid | 100.00 | 24.04 | 9.88 |
| Glutamic acid | 100.00 | 57.78 | 24.89 |
| Serine | 100.00 | 14.37 | 15.35 |
| Asparagine H$_2$O | 100.00 | 15.03 | 19.17 |
| Glycine | 100.00 | 103.55 | 90.58 |
| Glutamine | 100.00 | 19.26 | 23.14 |
| Histidine | 100.00 | 45.59 | 45.32 |
| Threonine | 100.00 | 63.09 | 61.39 |
| Arginine | 100.00 | 72.22 | 74.25 |
| Alanine | 100.00 | 1513.36 | 1518.46 |
| Proline | 100.00 | 58.54 | 55.36 |
| Tyrosine | 100.00 | 46.37 | 47.63 |
| Cystine | 100.00 | 53.43 | 56.39 |
| Valine | 100.00 | 42.75 | 42.11 |
| Methionine | 100.00 | 13.23 | 11.51 |
| Isoleucine | 100.00 | 48.39 | 48.79 |
| Leucine | 100.00 | 23.58 | 20.63 |
| Lysine HCl | 100.00 | 41.85 | 40.65 |
| Phenylalanine | 100.00 | 34.99 | 33.00 |
| Tryptophan %: | 100 | 69.1 | 68.8 |

BACD_24_06_014_026 . . . basic medium (s. materials and methods)

FUR_06/10_M04_K06 . . . Fermentation lot, 6$^{th}$ day of culture

FUR_06/10_M04_K07 . . . Fermentation lot, 7$^{th}$ day of culture

The peak area of the respective amino acid in the HPLC-diagram of the basic medium was set to 100%. By comparison to the peak area obtained on day 6 and 7 of the chemostat culture the decrease of the respective amino acid was determined.

Due to low glutamine concentrations in the supernatant of the culture, glutamine was added to the medium (300 mg/L) to give a final concentration of glutamine at 900 mg/L. After the addition of glutamine to the medium the growth rate increased from 0.55 d$^{-1}$ to 0.67 d$^{-1}$ (see Tables 13 and 14). By the addition of these three amino acids mentioned above (namely methionine (10 mg/L), leucine (40 mg/L) and phenylalanine (10 mg/L)) to the medium, the growth rate of the cells could be increased again (0.69 d$^{-1}$) (see Table 15). The volumetric productivity went up to approximately 267 kU/L/d (=+13%) and the specific productivity showed an increase of 16%. The supplementation of the medium with glutamine, methionine, leucine and phenylalanine showed a positive effect on cell growth, and volumetric and specific activity, and was therefore retained for further medium preparation.

TABLE 13

Fermentation data of the chemostat culture FUR_06/10-M04 from day 6 to day 9 of culture

| Experiment FUR_06/10-M04 | glc [g/L] | gln [g/L] | pH NOVA | D [1/d] | CC [1 E6/mL] | μ [1/d] | Furin [IU/mL] | P [kIU/L/d] | qP [IU/C/d]*10$^6$ |
|---|---|---|---|---|---|---|---|---|---|
| Day 6-9 | 1.58 | 0.10 | 7.16 | 0.494 | 2.35 | 0.548 | 306.55 | 151 | 64 |

TABLE 14:

Fermentation data of the chemostat culture FUR_06/10-M04 after the supplementation of the medium with of 300 mg/L glutamine on day 12

| Experiment FUR_06/10-M04 | glc [g/L] | gln [g/L] | pH NOVA | D [1/d] | CC [1 E6/mL] | μ [1/d] | Furin [IU/mL] | P [kIU/L/d] | qP [IU/C/d]*10$^6$ |
|---|---|---|---|---|---|---|---|---|---|
| Day 15-21 | 1.47 | 0.35 | 7.16 | 0.668 | 2.27 | 0.673 | 352.68 | 236 | 104 |

TABLE 15

Fermentation data of the chemostat culture FUR_06/10-M04 after the addition of methionine (10 mg/L), leucine (40 mg/L) and phenylalanine (10 mg/L) on day 22 to the medium

| Experiment FUR_06/10-M04 | glc [g/L] | gln [g/L] | pH NOVA | D [1/d] | CC [1 E6/mL] | μ [1/d] | Furin [IU/mL] | P [kIU/L/d] | qP [IU/C/d]*10$^6$ |
|---|---|---|---|---|---|---|---|---|---|
| Day 26-29 | 1.37 | 0.38 | 7.13 | 0.713 | 2.20 | 0.695 | 373.80 | 267 | 121 |

To check whether the supplemented amounts of the amino acids in the medium were sufficient, another amino acid analysis of a chemostat culture (10 L) was performed. The culture had been supplied with 300 mg/L glutamine and the respective amounts of the three amino acids. The samples were drawn on day 7 and 15 of culture, and the culture conditions were similar to those mentioned above. The results (see Table 16 where only the data for methionine, leucine and phenylalanine are shown) confirmed that sufficient amounts of the supplemented amino acids were present in the fermentation broth.

TABLE 16

Relative amount of methionine, leucine and phenylalanine in a chemostat culture (FUR 06/17_F04) supplemented with glutamine (300 mg/L), methionine (10 mg/L), leucine (40 mg/L) and phenylalanine (10 mg/L)

| Amino acid | Peak area [%] BACD-24-06-030-057 | relative peak area [%] FUR 06/17_F04-K07 | relative peak area [%] FUR 06/17_F04-K15 |
|---|---|---|---|
| Methionine | 100.0 | 47.5 | 61.7 |
| Leucine | 100.0 | 50.3 | 65.4 |
| Phenylalanine | 100.0 | 50.1 | 65.2 |

Reduction of the $NaHCO_3$ concentration and increase of the glucose concentration. The influence of high dissolved $CO_2$ concentrations in the cell culture on growth and productivity was investigated. Due to large scale production in a bioreactor, a greater $CO_2$ concentration in the cell culture can be expected than in 2.5-32 L bioreactors. Therefore, two fermentation runs were carried out in parallel, one run with a $CO_2$ concentration of approximately 7.5% and the other one with a $CO_2$ concentration of approximately 12%. The $CO_2$ concentration was adjusted by varying the $CO_2$ fraction in the head space flow. The $CO_2$ concentration in the cell culture was measured by analyzing drawn samples with the NOVA instrument. The fermentation was carried out at 37° C., at a pH of 7.15 and with a $pO_2$ of 20%.

A $CO_2$-concentration of 11-12% had a negative influence on cell growth and productivity. At this $CO_2$-concentration, a growth rate of 0.29 $d^{-1}$ was reached over an interval of 12 days at a cell count of $1.1 \times 10^6$ cells/mL and a dilution rate of 0.30 $d^{-1}$. In the fermentation run with approx. 7.5% $CO_2$, a growth rate of 0.52 $d^{-1}$ was reached at a cell count of $1.49 \times 10^6$ cells/mL and a dilution rate of 0.53 $d^{-1}$ in the same interval. At high $CO_2$ concentrations, the viability was reduced to 86.1%, compared to 95.9% at 7.5% $CO_2$. Additionally, the volumetric productivity was reduced to approximately 36% and the specific productivity to 50%. Due to the high $CO_2$ concentration, the specific glucose uptake rate was decreased as well (−39%). The negative influence of an increased $CO_2$ concentration (11-12%) on cell growth and productivity was quite obvious and, therefore, it is optimal to carry out the fermentation at 7.5% $CO_2$.

As set out above, experiments showed that when the concentration of $CO_2$ was increased to 12% in the 1,000 L bioreactor, a strong decrease in the performance of the CHO-Furin clone 488-3 can be expected. Therefore, it was decided to reduce the $NaHCO_3$ concentration in the medium from 2 g/L to 1.5 g/L. A lesser amount of $NaHCO_3$ in the medium also decreased the buffer capacity of the medium and, therefore, two fermentation runs (10 L) were compared, one with 3.15 g/L glucose and 2 g/L $NaHCO_3$ in the medium (FUR_06/24_F01) and another one with 4.65 g/L glucose and 1.5 g/L $NaHCO_3$ (FUR_06/26_F04).

To simulate the conditions of a large scale bioreactor (1,000 L), the concentration of dissolved $CO_2$ during fermentation was adjusted to 7-8% in the fermenter with 2 g/L $NaHCO_3$ and to 6-7% in the fermenter with 1.5 g/L $NaHCO_3$ by constant $CO_2$ gassing in the head space. The growth rates of both cultures were similar (0.58 and 0 56 $d^{-1}$) and the cultures showed comparable volumetric productivities and viabilities. However, the specific glucose uptake rate was slightly higher in the culture with a lower $NaHCO_3$ concentration (0.83 mg/$10^6$ cells/d vs. 0.67 mg/$10^6$ cells/d). Therefore, a glucose concentration of 4.65 g/L was considered to be reasonable and was retained in further medium preparation.

Investigation of the Synperonic F68 concentration in the Furin medium. The regular concentration of Synperonic F68 in the cell culture medium was set at 0.25 g/L. The purpose of Synperonic F68 in the medium is to protect the cells from damage due to submerged oxygenation. Therefore, one experiment was carried out in 2×10 L bioreactors, where an increased Synperonic F68 concentration of 1.0 g/L vs. the regular concentration of 0.25 g/L was investigated. The fermentation was carried out at 35.8° C. at a pH of 7.30 and with a $pO_2$ of 20%.

With increasing Pluronic concentration (Synperonic F68), a slightly higher specific growth rate and cell density could be achieved. Thus, due to increased specific productivity, a proportionally greater volumetric productivity of 365 vs. 278 kU/L/d could be achieved.

Supernatants from these experiments were collected and filtered with a depth filter (Cuno Cart.Z08P4A30SP 4 discs) followed by a membrane filter (Pall Fluorodyne II KA2DFLP2). The filtered supernatants were concentrated by ultrafiltration (Sartorius 30S1463901E-SG PSU 10KD, 0.2 $m^2$) and diafiltrated against the Furin diafiltration buffer. The sterile filtered concentrate (Sartorius Sartobran P 523130748-00 0.45/0.2µ) was purified on the Capto MMC column. Results from this purification experiments revealed that the increased Synperonic F68 has no detrimental influence on quality and/or purity of the purified rFurin. No elevated Synperonic F68 concentrations could be found in the eluate of the Capto MMC column, which were <0.15 mg/mL in both eluates.

Despite these results the Synperonic F68 concentration in the rFurin medium was kept at the original 0.25 g/L. However, in case of scale up problems due to submerged oxygenation, an increasing Synperonic concentration of up to 1.0 g/L could be considered, with the potential of increased yields without detrimental influence of the final Furin product.

Final Medium Composition for rFurin Production in Fermentation. Based on the medium optimization experiments, the following medium composition is shown to be optimal for the fermentation of CHO clone 488-3 in bioreactor cultures for the production of rFurin.

TABLE 17

Components of the basic medium and
optimized fermentation medium

| Component | Basic Medium Concentration [g/kg] | Optimized Medium Concentration [g/kg] |
|---|---|---|
| DMEM/F12(1:1) | 11.76 | 11.76 |
| L-Glutamine | 0.6 | 0.9 |
| D-Glucose | — | 1.5 |
| Ethanolamine | 0.00153 | 0.00153 |
| Synperonic | 0.25 | 0.25 |
| Putrescine•2HCl | 0.0036 | 0.0036 |
| Methionine | — | 0.01 |
| Leucine | — | 0.04 |
| Phenylalanine | — | 0.01 |
| FeSO4•7H2O | 0.0006 | 0.0006 |
| CuSO4•5H2O | 0.00000125 | 0.00000125 |
| NaHCO3 | 2.0 | 1.5 |

The influence of different $pO_2$ set points on growth rate and productivity was also investigated. Three different $pO_2$ set points were tested, i.e. 10%, 20% and 50%. The experiments were performed in 1.5 L bioreactors with gassing via head space. All fermentation runs were carried out at 35.1° C. at pH 7.20. Comparison of the fermentation runs at 10, 20 and 50% $pO_2$ showed a slight increase of the growth rates (0.59, 0.62 and 0.65 $d^{-1}$) with increasing $pO_2$ set points. Likewise, the volumetric productivity was greatest at 50% $pO_2$. The mean cell counts of the different fermentation runs were very similar. Thus, the increase in the volumetric productivity was the result of the increasing growth rate.

Consequently, a $pO_2$ set point of 50% seemed to influence the growth rate positively, and as a result the volumetric productivity was approx. 4% higher than at standard conditions (=20% $pO_2$). No effect on viability was observed. Therefore, a setpoint of pO2=20% and a range for regulation between 10%-50% could be confirmed to be suitable for fermentation of the CHO clone #488-3.

Figure 5:
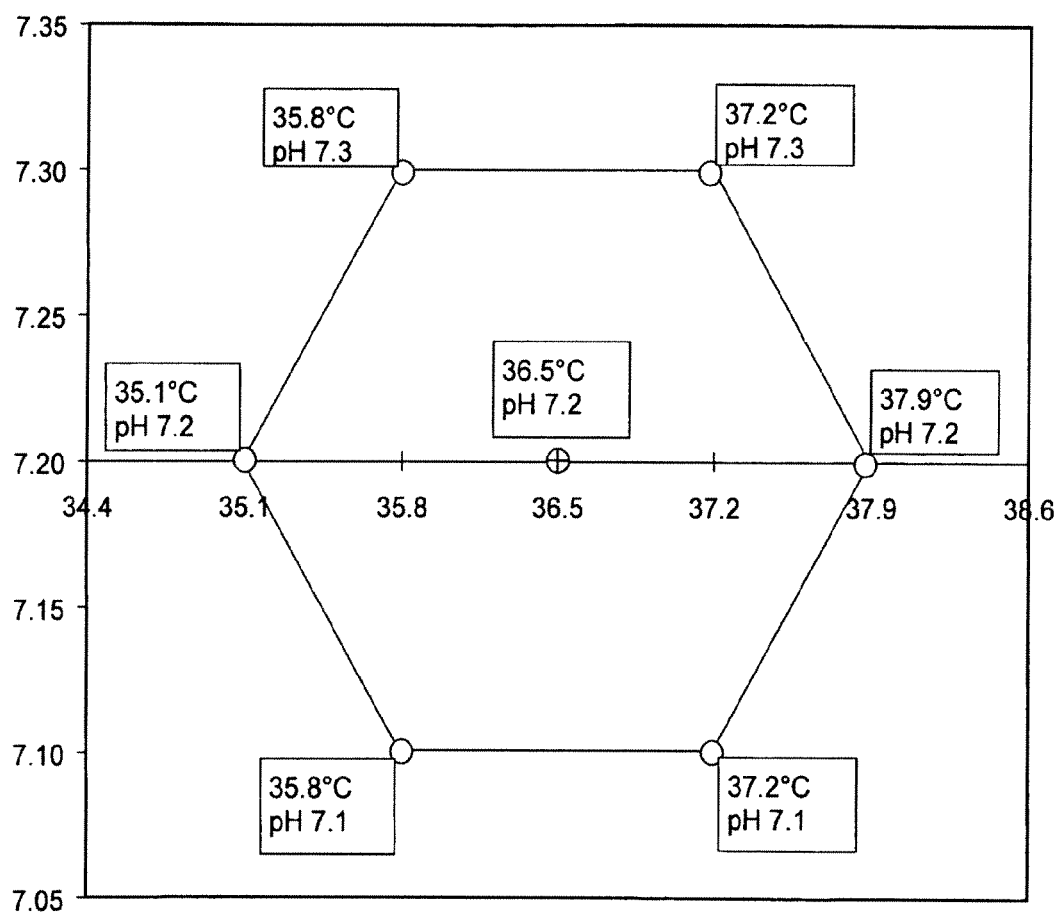
FIG. 5 shows a "Doehlert Matrix" where five temperatures were combined with three pH values, resulting in seven combinations of temperature and pH.

Optimization of temperature and pH to maximize the volumetric productivity. The influence of pH and temperature on the performance of the CHO-Furin clone was investigated. By using a 'design of experiments method', different temperatures were combined with different pH values to ascertain the conditions which resulted in maximum volumetric productivity. Five temperatures were combined with three pH values according to the "Doehlert Matrix", resulting in seven combinations of temperature and pH, as shown in FIG. 5.

The combination of 36.5° C. and pH 7.20 was chosen as the center point, which was applied to two fermentation lots. Table 18 sets out the culture conditions used in the different fermentation lots.

TABLE 18

Experimental setup of the Doehlert Matrix: Culture
conditions of the different fermentation lots

| Fermentation lot | Temp. [° C.] | pH |
|---|---|---|
| FUR_06/43-B07 | 35.1 | 7.20 |
| FUR_06/43-B05 | 35.8 | 7.10 |
| FUR_06/40-B03 | 35.8 | 7.30 |
| FUR_06/40-B01 | 36.5 | 7.20 |
| FUR_06/43-B02 | 36.5 | 7.20 |
| FUR_06/40-B08 | 37.2 | 7.10 |
| FUR_06/40-B04 | 37.2 | 7.30 |
| FUR_06/40-B06 | 37.9 | 7.20 |

TABLE 19

Mean values of the fermentation data of the fermentations
FUR_06/40-B01, -B03, -B04, -B06, -B08 and FUR_06/43-B02, -B05, -B07

| Fermentation lot | Temp. [°C] | pH | CC [$10^6$/mL] | μ [1/d] | Furin [IU/mL] | P[1] [kIU/L/d] | qP[1] [U/$10^6$/d] | Viability [%] |
|---|---|---|---|---|---|---|---|---|
| FUR_06/43-B07 | 35.1 | 7.20 | 1.74 | 0.595 | 930 | 543 | 312 | 97.7 |
| FUR_06/40-B03 | 35.8 | 7.30 | 1.64 | 0.632 | 621 | 379 | 232 | 97.6 |
| FUR_06/43-B05 | 35.8 | 7.10 | 1.73 | 0.647 | 683 | 429 | 250 | 98.5 |
| FUR_06/40-B01 | 36.5 | 7.20 | 1.78 | 0.696 | 439 | 309 | 174 | 97.9 |
| FUR_06/43-B02 | 36.5 | 7.20 | 1.66 | 0.684 | 454 | 310 | 186 | 96.8 |
| FUR_06/40-B04 | 37.2 | 7.30 | 1.71 | 0.642 | 284 | 184 | 108 | 96.8 |
| FUR_06/40-B08 | 37.2 | 7.10 | 1.68 | 0.652 | 338 | 215 | 128 | 98.3 |
| FUR_06/40-B06 | 37.9 | 7.20 | 1.52 | 0.473 | 143 | 65 | 43 | 96.1 |

[1] the mean volumetric and the mean specific productivity over 5 culture days were calculated by forming the the mean value of the singel productivities The data were analyzed statistically with the Response Surface Methodology (RSM), using the "Minitab" software. RSM explores the relationships between several explanatory variables and one or more response variables. The main idea of RSM is to use a set of designed experiments to obtain an optimal response. The analysis focused on the volumetric and specific productivity as well as on the growth rate.

Figure 6:
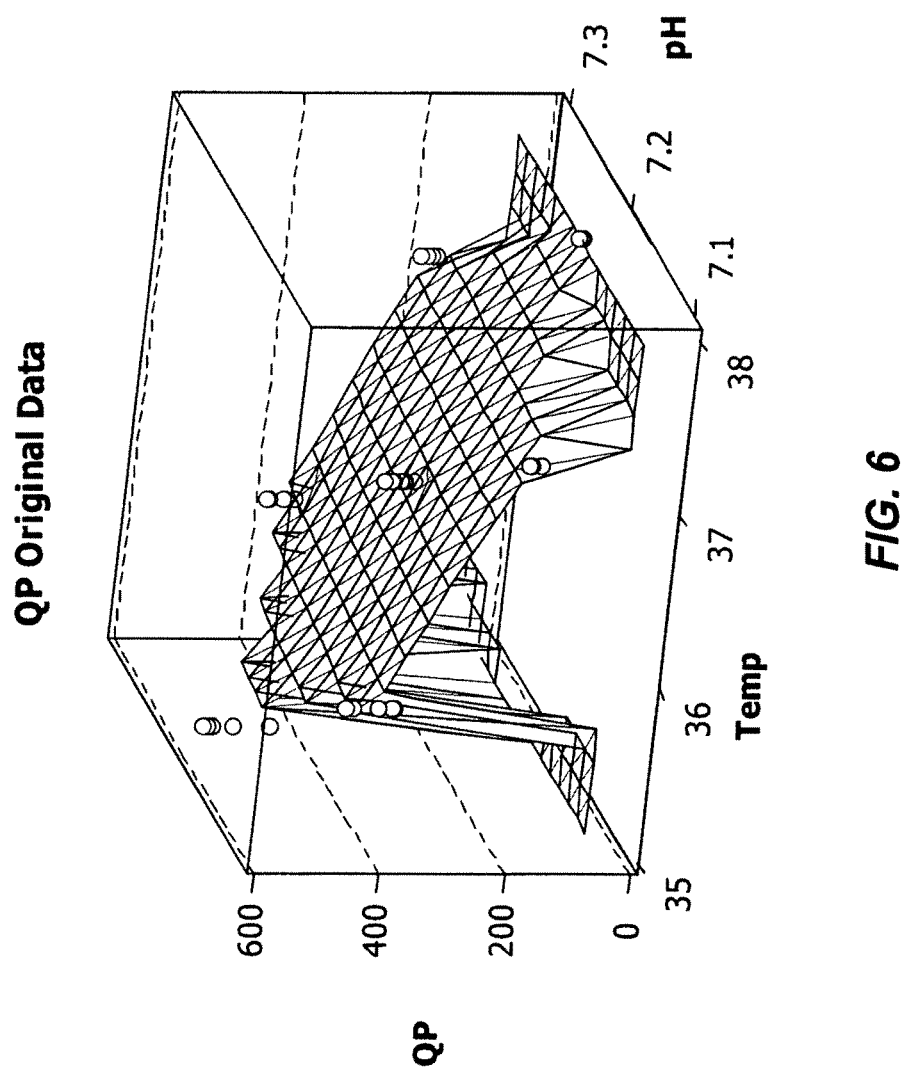
FIG. 6 shows a surface plot analysis of the data in reference to the volumetric productivity. The coordinates of the data in FIG. 6 are marked as points. The surface shows the assumed correlation of the single data.

Analysis of the data in reference to the volumetric productivity. As a first step, a surface plot was created (FIG. 6). The coordinates of the data in FIG. 6 are marked as points. The surface shows the assumed correlation of the single data.

The surface plot supposes a linear correlation between the parameters temperature/pH and the responding volumetric productivity. The chart indicates an increase of the volumetric productivity with decreasing temperature. The influence of the pH is considered to be weak. Subsequent calculations showed a linear correlation of the data (calculation not shown). By variance analysis, an equation was generated which describes the correlation between pH, temperature and volumetric productivity:

$$P = 7693.1 - 162.4 * \text{Temp} - 202.8 * \text{pH}$$

Figure 7:
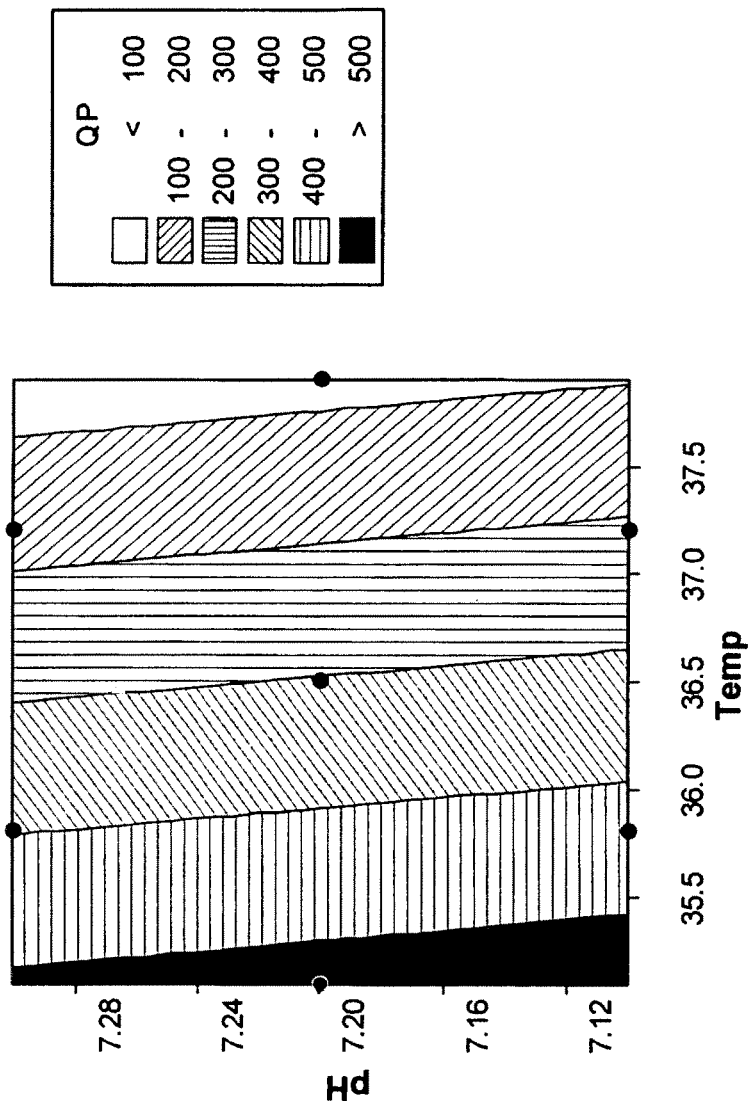
FIG. 7 shows a contour plot which illustrates the influence of temperature and pH on the volumetric productivity. The dots indicate the conditions (pH/temp.) which had been tested experimentally.

Based on the mathematical model a contour plot was generated (FIG. 7) which illustrates the influence of temperature and pH on the volumetric productivity. The dots indicate the conditions (pH/temp.) which had been tested experimentally.

The contour plot shows that the area, where maximum volumetric productivity can be expected, is at 35.1° C. and a pH of approx. 7.10. Both values are at the edge of the experimental design which means that the real maximum could be found even below those values. Furthermore the Contour plot shows that the influence of the pH on the volumetric productivity is marginal and slightly higher at low pH values.

Figure 8:
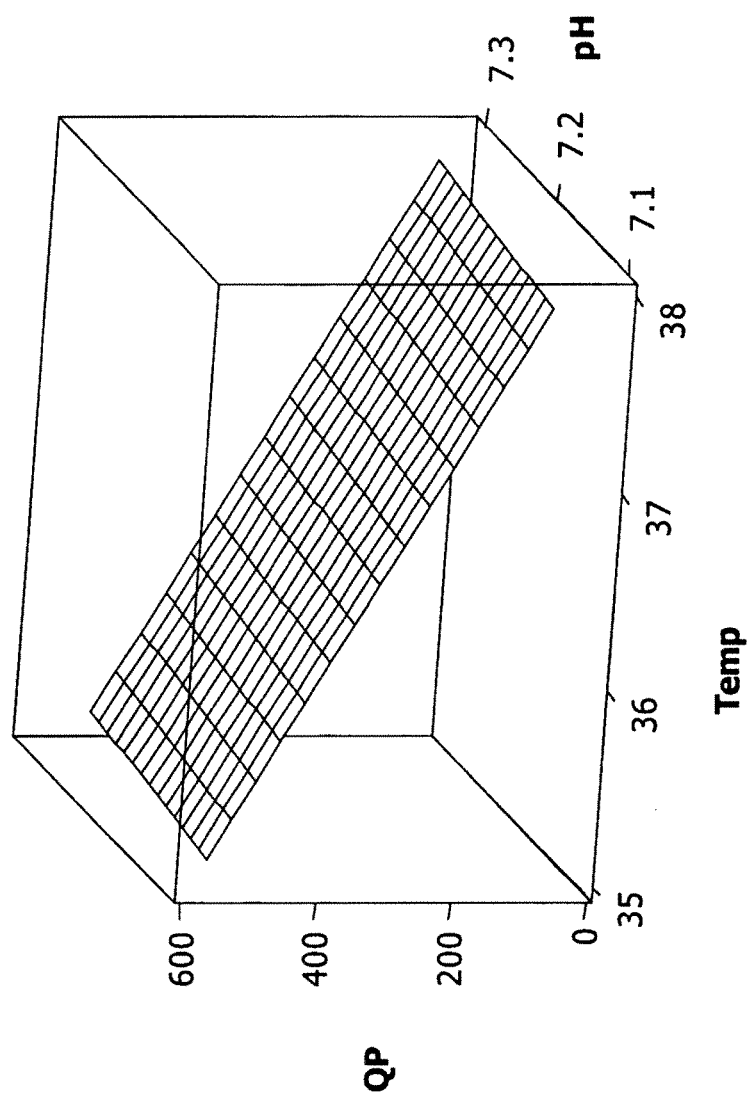
FIG. 8 shows a surface plot which is a three-dimensional illustration demonstrating the strong influence of the temperature and the weak influence of the pH on the volumetric productivity.

The surface plot (FIG. 8) which is a three-dimensional illustration of the mathematical model, gives the same result as the contour plot: the strong influence of the temperature and the weak influence of the pH on the volumetric productivity.

Analysis of the data in reference to the growth rate p. The correlation of the growth rate with temperature and pH is described in a quadratic equation. Again, a strong influence of the temperature and a weak influence of the pH can be found. Strong variation of the growth rate hampers the design of a mathematical model. Analysis of variance and regression gave following equation:

$$P=-103.539+5.706*Temp-0.079*Temp^2-0.233*pH-0.020*pH^2$$

The influence of the pH on the growth rate is statistically not ascertainable, as indicated by the high P-value for the pH-terms which was calculated to be 0.99 (calculation not shown).

Figure 9:
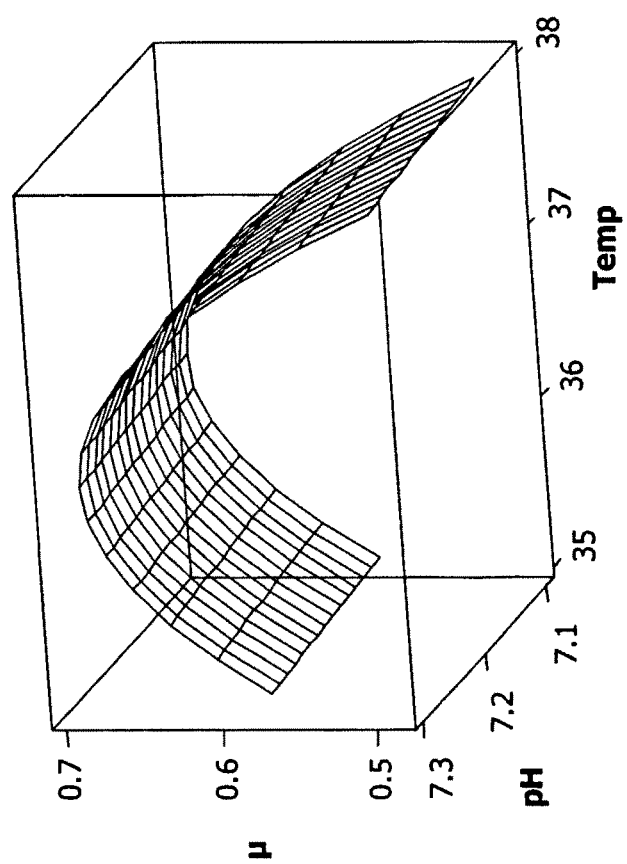
FIG. 9 shows a surface plot which illustrates the modeled correlation three-dimensionally; it demonstrates the quadratic relationship and shows clearly a maximum for the growth rate at 36.5° C.

The surface plot (FIG. 9) illustrates the modeled correlation three-dimensionally, demonstrates the quadratic relationship, and shows a maximum growth rate at 36.5° C.

Figure 10:
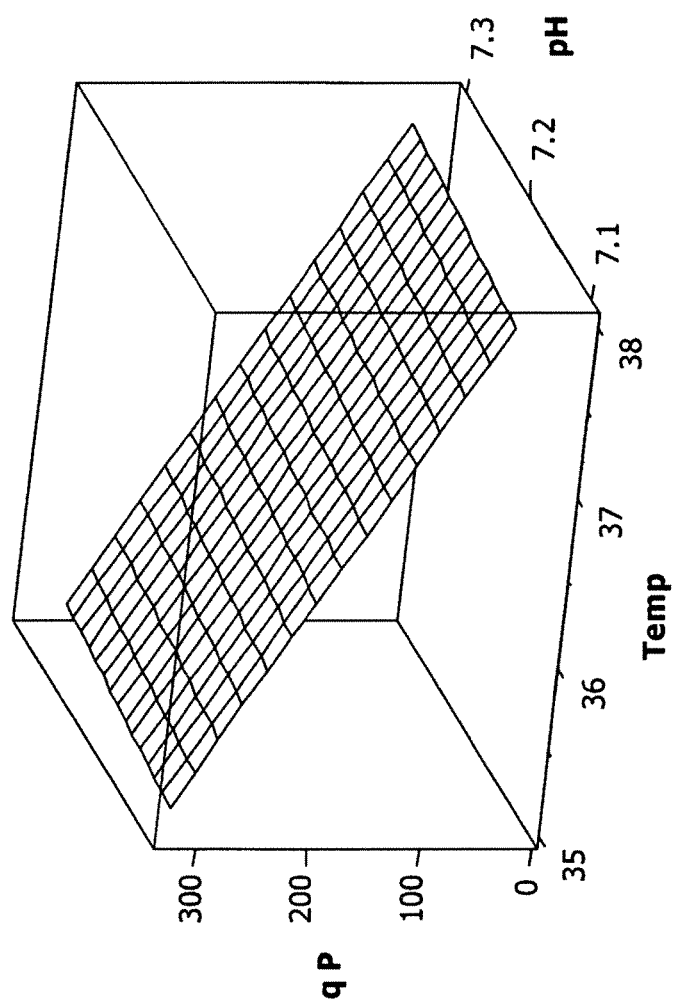
FIG. 10 sets out an analysis of the data in reference to specific productivity. There is a similar correlation of the specific productivity with temperature and pH as seen for the volumetric productivity.

Analysis of the data shows a similar correlation of the specific productivity with temperature and pH as seen for the volumetric productivity (FIG. 10). The correlation is described by a linear equation. The influence of the pH is again low as proved by variance analysis (calculation not shown):

$$qP=4261.40-93.35*temp-93.77*pH$$

Figure 11:
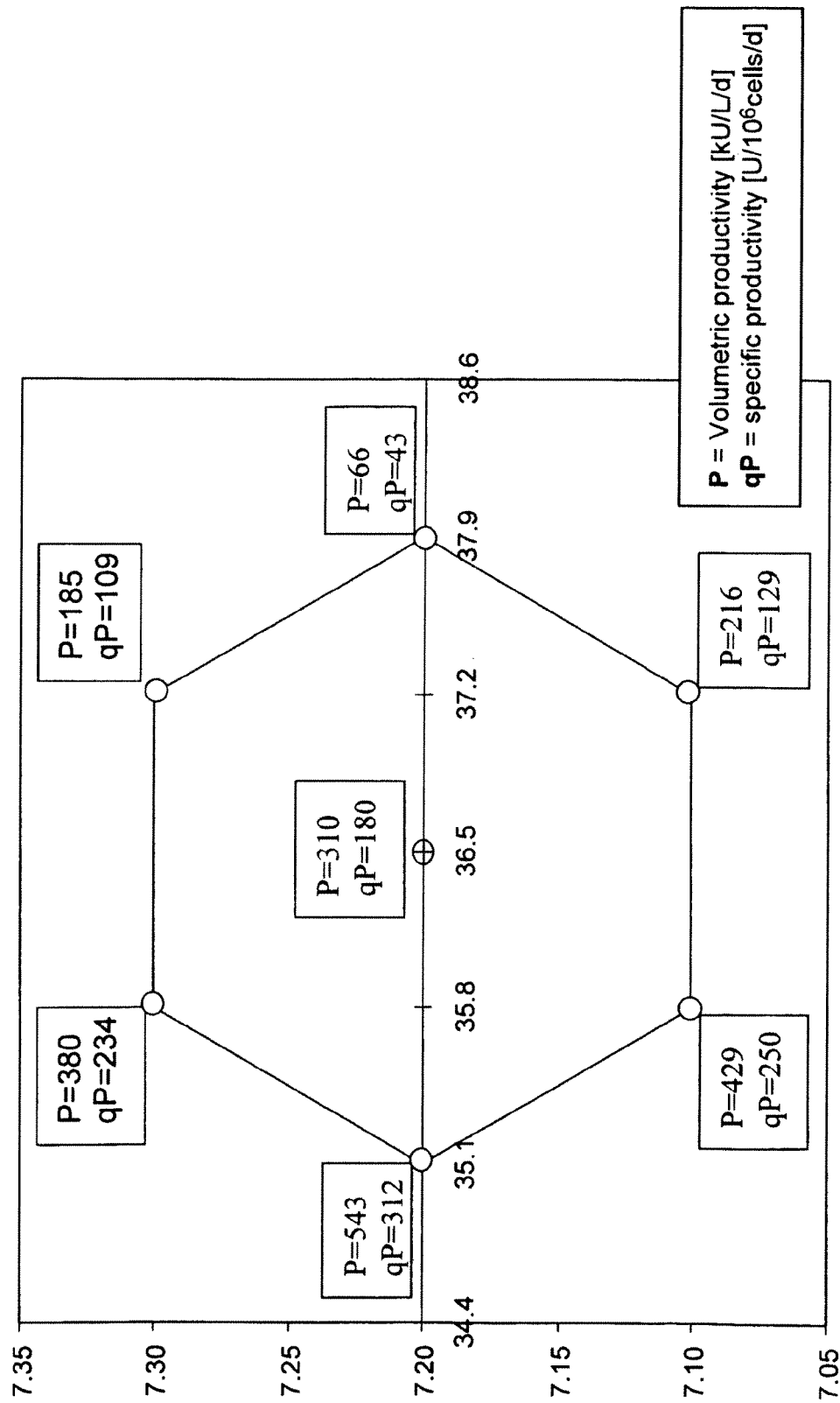
FIG. 11 shows that by decreasing the temperature from 37° C. to 35.1° C., the volumetric productivity could be increased from approx. 200 kU/L/d to 540 kU/L/d.

In summary, the experiments for optimization of temperature and pH and subsequent analysis of the data gave a quite clear result. The greatest volumetric productivity, which is considered as the most important parameter for process optimization, was achieved by culture at the lowest temperature (35.1° C.) and lowest pH (7.10). The influence of pH is statistically hardly significant, and a pH value between 7.10 and 7.30 would give very similar results. By decreasing the temperature from 37° C. to 35.1° C., the volumetric productivity could be raised from approx. 200 kU/L/d to 540 kU/L/d which is 2.7 times greater (FIG. 11). Based on these results, the new set points for temperature and pH, for the culture of the CHO-Furin clone in the chemostat mode, were determined as 35.1° C. and 7.15.

Comparison of chemostat mode to batch refeed mode. The culture of the CHO-Furin clone in the chemostat mode at a low temperature (35.1° C.) resulted in high yields in small scale experiments (1.5 L, 2.5 L, 10 L and 32 L) and was considered to be the appropriate culture method for the large scale culture for production of rFurin. However, initial fermentation runs in the large scale (1200 L bioreactor in the PP1 facility) showed a strong decrease of the growth rate at the chemostat mode. As an alternative, to get higher growth rates, the batch reefed mode was set up in the large scale. Experiments in the 10 L bioreactor scale were carried out to compare growth and productivity in the chemostat mode with the batch reefed mode. The cells were cultured at 36.5° C. at a pH of 7.15 and a pO$_2$ of 20%. The batch was split to a cell count of 0.6-0.7×10$^6$ cells/mL every second culture day.

The chemostat- and the batch reefed-fermentations were run in parallel, using the same cell culture as inoculum. The cells were cultured in the chemostat mode until day 6. Then one fermentation run was switched to the batch refeed mode (FUR_06_50-F03) while the other one was continued in the chemostat mode (FUR_06_51-F04). Culture in the batch refeed mode resulted in a mean cell count of 2.22×10$^6$ cells/mL at the end of the batch, with a growth rate of 0.64 d$^{-1}$ (Table 20). In the chemostat mode, a growth rate of 0.50 d$^{-1}$ was obtained with an average cell count of 1.67×10$^6$ cells/mL. Due to the higher cell count and growth rate in the batch refeed mode, the volumetric productivity was greater as well (238 vs. 197 kU/L/d).

The data indicate that the batch reefed mode is a preferable culture method for the CHO-Furin clone in the 10 L scale, which results in even slightly higher volumetric productivities than in the chemostat mode (at 36.5° C. and a pH of 7.15). However, in the batch refeed mode, harvest- and further downstream processes are restricted to certain intervals, while in the chemostat mode, harvesting can be performed continuously. Thus, each method has its advantages. No optimization experiments for the parameters of the batch reefed mode were performed like for the optimal cell counts at the end of a batch or for the best split ratio.

TABLE 20

Mean values of the fermentation data from the fermentation runs FUR_06_51-F04 (Chemostat) and Fur_06_50-F03 (Batch Refeed)

| Ferment. lot | Vol. | Mode | D [1/d] | μ [1/d] | CC [1 E6/mL] | Furin [IU/mL] | P [kIU/L/d] |
| --- | --- | --- | --- | --- | --- | --- | --- |
| FUR_06_51-F04 | 10 L | chemostat | 0.494 | 0.497 | 1.67 | 401.4 | 198 |
| FUR_06_50-F03 | 10 L | batch refeed | — | 0.637 | 2.22 (end)[1] | 539.8 | 238[2] |

[1] Mean value of the cell counts at the end of each batch (2 batches)
[2] Mean value of the productivities at the end of each batch (2 batches)

Scale Up Investigations. Comparison of Rushton type-versus ball type-impellers at different agitation rates. The influence of the agitator type on growth rate and productivity was investigated. The standard setting used in the bioreactors for experiments with the CHO-Furin clone comprised a Rushton impeller and four baffle plates. The 1,000 L bioreactor for rFurin production was equipped with three pairs of ball impellers without any baffle plates. Therefore, an experiment was carried out to test three different settings in 10 L bioreactors: one reactor was equipped with the standard setting, another reactor with two pairs of ball impellers and no baffle plates, and a third reactor was assembled like the standard one but the agitation rate was reduced from 170 rpm to 90 rpm.

Table 21 gives an overview of the bioreactor set-ups. The agitation rate of 60 rpm with ball impellers gave a similar tip speed as the rushton impeller at 90 rpm (see Table 21). However, the tip speeds cannot be equated with each other due to the different geometry of the impellers (shape, diameter).

TABLE 21

10 L Bioreactor Set-ups for impeller/agitation rate experiment

| Fermentation lot | Impeller type/diam. | Levels | Baffle plates | Agitation rate | Tip speed |
|---|---|---|---|---|---|
| FUR_06/37_F03 | Rushton 80 mm | 2 | 4 | 170 | 0.712 m s$^{-1}$ |
| FUR_06/35_F01 | Rushton 80 mm | 2 | 4 | 90 | 0.377 m s$^{-1}$ |
| FUR_06/38_F04 | Ball 140 mm, 39.5 mm diameter | 2 | — | 60 | 0.440 m s$^{-1}$ |

The fermentation conditions were as follows: 37° C., pH 7.15, pO$_2$ of 20% and pCO$_2$ of 6-7%. (Medium: 4.65 g/L Glc, 1.5 g/L NaHCO$_3$). Comparison of the fermentation data showed that the performance in the bioreactor with the standard set-up, i.e. equipped with the rushton impeller and agitated at a rate of 170 rpm, was higher than in the bioreactors with the other set-ups (Table 22). The use of ball impellers at 60 rpm resulted in a somewhat lower growth rate (0.57 vs. 0.61d-1), a lower volumetric (197 vs. 227 kU/L/D) compared to the rushton impeller at 170 rpm. The viability was hardly affected though. Using a rushton-impeller stirred bioreactor at an agitation rate of 90 rpm instead of 170 rpm clearly diminished the growth rate (0.54 vs. 0.61 d-1), volumetric productivity (175 vs. 227 kU/L/D) and cell specific productivity (115 vs. 138 U/10$^6$ cells/day).

The data from this experiment showed that both, a ball impeller at 60 rpm and Rushton impellers at a reduced agitation rate, result in a declined performance of the CHO-Furin clone compared to the Rushton impellers at 170 rpm. Nevertheless, the results also revealed that it is possible to use a ball impeller for culture of the CHO-Furin clone. Among the set-ups which were tested, the set-up with the rushton impeller at 170 rpm plus four baffle plates displayed the roughest conditions. Notably, however, no decrease of cell viability was observed under these conditions, which indicates a high mechanical resistance of the investigated CHO-Furin clone.

TABLE 22

Mean values of the fermentation data of three fermentation runs of the CHO-Furin clone in bioreactors with different set-ups (impeller type, baffle plates)

| Fermentation lot | Set-up | CC [10$^6$/ml] | D [d$^{-1}$] | Furin [IU/mL] | μ [d$^{-1}$] | P [kU/L/d] | qP [U/10$^6$/d] | Viability [%] |
|---|---|---|---|---|---|---|---|---|
| FUR_06/37_F03 | Rushton 170 rpm | 1.65 | 0.628 | 361.37 | 0.614 | 227 | 138 | 95.4 |
| FUR_06/38_F04 | Ball impeller 60 rpm | 1.52 | 0.600 | 328.10 | 0.568 | 197 | 130 | 94.1 |
| FUR_06/35_F01 | Rushton 90 rpm | 1.53 | 0.574 | 305.31 | 0.544 | 175 | 115 | 94.3 |

Comparison of different agitation rates with pitched blade impellers in 32 L bioreactors. For the GMP run campaign ORFURFB07002 in the PP1 the bioreactor (working volume 950 L) was equipped with a pitched blade impeller type (2 pcs., d=700 mm) instead of the previously used ball type impellers.

2 day batch reefed cycles were carried out during this campaign. In order to assess this change compared to the previous campaigns, a 32 L bioreactor was set up with a similar type of pitched blade impellers (1 piece, d=140 mm), and fermentations were carried out using cell suspension from the PP1 facility and medium to ensure comparable materials to be used.

A similar batch reefed process was carried out, where a 2-3 consecutive two day batch cycles were started with a starting cell density of 0.5×10E06 cells/mL. The experiment was carried out at 2 different agitation rates, i.e. 55 rpm and 120 rpm). Culture conditions were identical with the culture conditions used in the PP1: pH-SP 7.15, Temp-SP 35.5° C., pO2-SP 20%. Data from the last batch were compared after adaptation to the respective agitation conditions.

TABLE 23

Growth rate, cell count and vol. productivity of the batches of run FUR_07/06-F07 with pitched blade impellers in the 32 L bioreactor

| FUR_07/06-F071 Intervall | Agitation rate [rpm] | CC [1]) [10$^6$/ml] | Split [2]) 1:x | Furin [IU/mL] | μ [d$^{-1}$] | P [3]) [kU/L/d] |
|---|---|---|---|---|---|---|
| Batch K02-K04 | 120 | 1.95 | 3.89 | 1197.8 | 0.680 | 445 |
| K10-K12 | 50 | 1.50 | 3.13 | 812.0 | 0.570 | 276 |

[1]) cell count at the end of each batch

[2]) theoretical split ratio to be applied in a 2 batch reefed process: split ratio = e^(2 × μ)

[3]) calculation of volumetric productivity: P = (1 − (1/split ratio)) × product titer/2 days The experiment demonstrated again the effect of agitation conditions on specific growth rates of the CHO clone #488-3. The increasing growth rates led to greater final cell densities at the end of the batch, when applying the same starting cell densities. Volumetric productivities increased from 276 kU/L/D to 445 kU/L/D (+61%), whereas the final cell density increased by 30% (1.95 vs. 1.5×10E06 cells/mL). These results indicate that the increased agitation rate had a positive impact on cell-specific productivity.

It also might be concluded that fermentation runs, which resulted in average productivities of around 200 kU/L/D were mainly a result of the applied low agitation rates of 20 rpm, and not due to the impeller design itself. Here it could be demonstrated, that pitched blade impellers can result in yields >400 kU/L/D, if the agitation rates are adjusted accordingly.

Example 4

Purification of Recombinant Furin (rFurin)

This example provides methods for the filtering and purifying rFurin. The collected cell culture supernatants were first filtered on depth filters (Cuno Zetaplus filters) to get them cell-free and particle-free, followed by membrane filtration at 0.45 μm PVDF filters (PALL Fluorodyne II). The filtered cell culture supernatant containing the rFurin was then concentrated by ultrafiltration on 10 K PES UF cassettes from Sartorius (Sartocon PESU 10 kDa) with concentration factors ranging from 10-50. The furin concentrates (with furin activity ranging from 290-1700 Units/ml) were then stored in aliquots at <−60° C.

In an effort to get a more homogeneous rFurin preparation for use in the VWF maturation process, experiments were conducted to partially purify the rFurin from the cell culture supernatant. A partially purified rFurin reagent is easier to use for characterization and release testing. It also results in a reduced presence of CHO host cell proteins in the VWF maturation process.

A purification procedure on an anion exchange resin was developed that required a loading conductivity of <5 mS/cm (RT) for efficient binding of rFurin. The elution was then performed as a step procedure at an ionic strength of approximately 500-300 mM NaCl and during the screening phase, a gradient elution up to 300 mM NaCl was applied (see overview in Table 24). The original pH of the buffers of 6.7 (RT) was increased to 7.5 to improve binding of rFurin during loading, in particular at high protein loading and high liner flow rates (see summary of relevant buffers in Table 25). The purification experiments were performed on EMD TMAE (Merck) and CaptoQ (GE Healthcare) anion exchange resins that differed in the stability of the packed and the maximum flow rate to operate. The analytical data summarized in Table 26 show that rFurin can be concentrated from the cell culture supernatant up to 362 fold with yields ranging from 20-71%. The rFurin activities in the eluate pools was between 639 Units/ml and 27651 Units/ml depending on the load applied. The CHO impurity level in the eluate was found in a range between 10-134 ng CHO protein/Unit rFurin and reduction rates up to 12.3 with a slightly better performance for CHO reduction found for the CaptoQ resin.

In summary, purification of rFurin by anion exchange chromatography proved to be an option for concentration, which is important for storage of the rFurin reagent at <−60° C. In addition, a slight CHO reduction by a factor from 3-12 is important in reducing the concentration of CHO protein in the preparation of VWF.

TABLE 24

Approximate procedure for the purification of rFurin on anion exchange resin.

| Step | Buffer | CV | Flow rate [cm/h] | comment |
|---|---|---|---|---|
| Equilibration | FEQ buffer | 10 | 150-600 | |
| Load | CCS diluted with EQ1 | up to 1200 | | Conductivity of the load ≤5 mS/cm; |
| Wash 1 | EQ buffer | up to 50 | | Optional; at high column |
| Wash 2 | Mix of EQ buffer and FEL buffer | Approx. 10 | | loading this step was omitted |
| Step Elution | 30% FEL/70% FEQ | 14 | 75-300 | |
| Gradient elution | 100% FEQ - 30% FEL/70% FEQ | 14 | 75-300 | Optional: used for initial screening experiments |
| Post conditioning | Various buffers (FEL, NaCl buffer, CIP buffer) | 15 | n.d. | |

For EMD TMAE (Merck) the flow rate applied was 150/75 cm/h, for CaptoQ (GE Healthcare) the flow rate was 600/300.

TABLE 25

Buffers for the purification of furin on anion exchange resin

| Buffer | formulation | |
|---|---|---|
| Equilibration buffer (FEQ) | 50 mM HEPES, 1 mM CaCl$_2$, pH = 6.7-7.5 at RT | At high loadings the pH of the buffers were increased to improve binding |
| Elution buffer (FEL) | 50 mM HEPES, 1 mM CaCl$_2$, 1M NaCl, pH = 6.7-7.5 at RT | |
| NaCl buffer | 2M NaCl | |
| CIP buffer | 0.5M NaOH | |

TABLE 26

Summary of relevant purification experiments of rFurin on anion exchange resin. The total protein content was determined using a Bradford assay. The CHO reduction rate is calculated as CHO protein loaded divided by total CHO protein found in the eluate pool.

| | Load | | | Eluate | | | | |
|---|---|---|---|---|---|---|---|---|
| | Column load U | Furin | | Conc. Factor Vol | yield | CHO | | |
| Run ID | Furin/ml resin | U/ml | U/mg protein | load/Vol eluate | % Furin activity | ng/U Furin | reduction | comment |
| 011 | 2705 | 639 | n.d. | 32 | 36 | 134 | 3.6 | TMAE; RT, elution 500 mM NaCl |
| 013 | 4016 | 2259 | n.d. | 33 | 57 | 51 | 3.0 | TMAE; RT, elution 400 mM NaCl |
| 015 | 4403 | 2007 | n.d. | 41 | 46 | 50 | 3.8 | TMAE; RT, elution 300 mM NaCl |
| 018 | 10635 | 2584 | n.d. | 65 | 37 | 41 | 6.5 | TMAE; RT, elution 300 mM NaCl |
| 021 | 8684 | 3550 | n.d. | 126 | 20 | 59 | 5.5 | TMAE; RT, elution 300 mM NaCl |
| 024 | 4151 | 903 | n.d. | 19 | 54 | 38 | 6.3 | CaptoQ; RT; elution 300 mM NaCl |
| 025 E1E2 | 15696 | 6185 | n.d. | | 45 | 10 | 12.3 | CaptoQ; RT; gradient elution |
| | | 1068 | n.d. | | 12 | n.d. | n.d. | |
| 026 E1E2 | 31316 | 10237 | 14138 | | 51 | 8 | 10.1 | CaptoQ; 4° C.; gradient elution |
| | | 1868 | n.d. | | 17 | n.d. | n.d. | |
| 028 | 32635 | 27651 | 10011 | 288 | 68 | 19 | 3.6 | TMAE; 4° C.; elution 300 mM NaCl |
| 029C | 23682 | 12642 | 7789 | 176 | 71 | 14.4 | 6.9 | CaptoQ; RT; elution 300 mM NaCl |
| 029T | 23806 | 14922 | 2671 | 362 | 30 | 65.1 | 3.3 | TMAE; RT, elution 300 mM NaCl |
| 033 | 20625 | 6843 | 4568 | n.d. | 35 | n.d. | 4.6 | CaptoQ; RT; elution 300 mM NaCl; load UF/DF conc. |
| 035 | 26244 | 13200 | 6967 | n.d. | 78 | n.d. | 1.9 | TMAE; RT, elution 300 mM NaCl; load UF/DF conc. |

Example 5

Concentration, Purification, and Analysis of rFurin

This example describes other methods used in the concentration and purification (i.e., downstream processing) of large-scale rFurin. Such processing methods include ultrafiltration, diafiltration, and capto-MMC chromatography, that was carried out in the production of substantially animal protein-free rFurin. It also describes methods of analyzing protein concentration, specific activity, and contamination by host cell protein and DNA.

Ultrafiltration. The supernatant (approx. 800-1200 kg in the Chemostat campaigns, and approx. 550-700 kg in the RFB-campaigns) was separated from the cells and concentrated to a final volume of 35-45 L by ultrafiltration. The parameters and setpoints of the Ultrafiltration/Diafiltration System (UFS) during the concentration step are listed in Table 27.

TABLE 27

Operating Parameters and Setpoints for the Concentration step

| Parameter | Setpoint |
|---|---|
| Temperature of the filtered harvest | 10-15° C. |
| Filter Area | 14 m$^2$ |
| Feed Pressure | 0.9-1.5 bar |
| Retentate Pressure | 0.7-1.2 bar |
| Permeate Pressure | 0-0.1 bar |
| Transmembrane Pressure | 0.7-1.0 bar |
| Specific Cross Flow Rate (Feed flow rate) | 300-600 L/h/m$^2$ |
| Specific Permeate Flow Rate | 15-40 L/h/m$^2$ |
| Concentration factor | 20-30 |
| Processing Time | 3-4 h |

Diafiltration. Immediately after finishing the concentration step, diafiltration of the retentate was initiated. The parameters and setpoints of the UFS during the diafiltration step are listed in Table 28.

TABLE 28

Operating Parameters and Setpoints for the Diafiltration Step

| Parameter | Setpoint |
|---|---|
| Filter Area | 14 m$^2$ |
| Feed Pressure | 0.9-1.5 bar |
| Retentate Pressure | 0.7-1.2 bar |
| Permeate Pressure | 0-0.1 bar |
| Transmembrane Pressure | 0.7-1.1 bar |
| Specific Cross Flow Rate (Feed flow rate) | 300-600 L/h/m$^2$ |
| Specific Permeate Flow Rate | 7-20 L/h/m$^2$ |
| Target Conductivity | <2 mS/cm |
| Diafiltration rate ($v_{permeate}/v_{retentate}$) | 4-5.5 |
| Processing Time[1] | 0.75-1.25 h |

When the conductivity of the retentate has fallen below 2 mS/cm (determined with the inline conductivity probe of the UFS), this process step was finished. This low conductivity is required to ensure a quantitative binding of the rFurin to the chromatographic gel in the subsequent purification step. The diafiltered product was transferred and the pH-value of the diafiltered product was adjusted to 6.0 by adding a 1 M acetic acid solution. The product was stored at room temperature (RT) before applying to the Capto-MMC column.

Capto-MMC Chromatography. The Capto-MMC gel, a multimodal cation exchanger, was used to bind rFurin and to eliminate the vast majority of contaminants from the diafiltrated product. After equilibration of the chromatography gel, the diafiltered product is loaded to the column. A 0.22 μm filter capsule was installed to perform an online filtration of the diafiltered product. The further chromatographic steps are listed and detailed in Table 29.

TABLE 29

Capto-MMC Chromatography Steps

| | Chromatography step | Buffer/Product | Linear flow rate cm/h | Quantity CV[1] |
|---|---|---|---|---|
| 1 | Acid wash | ES4 online diluted to 0.2M acetic acid | 300 | 1 |
| 2 | Equilibration | EP2 | 150 | 37 |
| 3 | Absorption | 35-45 L diafiltered product | 150 | |
| 4 | Equilibration | EP2 | 150 | 30 |
| 5 | Washing | WPF | 150 | 10 |
| 6 | Gradient Elution | EL1/MMC eluate | 150 | 15 |
| 7 | Elution II | EL2/MMC eluate II | 150 | 10 |
| 8 | Regeneration | ES4 | 150 | 10 |
| 9 | Regeneration | SHD | 150 | 10 |

[1]CV = column volume: volume of the packed resin in the chromatography column

In the downstream processing, no issues were observed. The downstream steps (Filtration, UF, DF) could be carried out at the same conditions used for the harvests from the Chemostat culture. Mean total rFurin activities yields of 91% (Campaign ORFU06002), 66% (Campaign ORFU07001) and 84% (Campaign ORFU07002) could be achieved. The only minor change is given by the fact, that the starting volume for the UF-step is somewhat lower compared to continuous culture. But this change has no effect on the quality of the purified product. (See data on total activity, Host Cell DNA, Host Cell Protein; see Table 30).

The mean values of all three campaigns for the Host Cell Protein and Host Cell DNA content reveal rather low mean maximum values of 8.55 μg/ml (ranging from 2.2-10.4 μg/ml) and 13.48 ng/ml (ranging from 0.0-23.9 ng/ml), respectively (see Table 30). The chromatographic step was able to reduce the specific contamination to low mean maximum values of 0.35 ng CHO Protein/U rFurin Activity (ranging from 0.13-0.52 ng CHO Protein/U) and 0.148 pg Host Cell DNA/U rFurin Activity (ranging from 0.0-0.365 pg DNA/U rFurin Activity).

TABLE 30

Capto-MMC Chromatography impurity results - Campaign comparison

| campaign | CHO-Protein Content μg/mL | CHO-Protein/ rFurin Activity ng/U | Host Cell DNA Content ng/mL | Host Cell DNA/rFurin Activity pg/U |
|---|---|---|---|---|
| ORFU06002 | 8.55 | 0.22 | 1.66 | 0.059 |
| ORFU07001 | 3.50 | 0.35 | 2.54 | 0.031 |
| ORFU07002 | 2.36 | 0.026 | 13.48 | 0.148 |

Furin Characterization. The quality and functionality of rFurin was assessed by following biochemical/biophysical methods (Table 31).

TABLE 31

Analytical methods for rFurin

| Method | Aim | Comment |
| --- | --- | --- |
| Fluorescent substrate cleavage | Enzyme activity | Low molecular weight substrate |
| Furin use test | Enzyme activity, maturation efficacy | rVWF substrate |
| SDS-PAGE | Protein composition | Western blot assay |
| IEF | Protein composition | Coomassie staining, Western blot assay |
| RP-HPLC | Protein composition | Protein fingerprint |

Furin Activity Assay. The purified rFurin batches (Capto-MMC eluate pools) were tested for enzymatic activity of Furin. The substrate is a short synthetic peptide containing the dibasic recognition sequence attached to a fluorescent aminomethyl coumarin (AMC) group, that is released after cleavage (BOC-RVRR-AMC). The released fluorogenic group can be detected by excitation at 380 nm and subsequent measurement of the emitted light at 435 nm. One activity unit is defined as the release of 1 pMol of AMC per minute at 30° C.

Depending on the fermentation and purification efficacy the measured values of rFurin activity were in the range of about 10000 U/ml up to more than about 100000 U/ml, with a mean value of approx. 69000 U/ml (Table 32, Table 32, and Table 34). An increase of rFurin activity for the RFB mode campaigns was noticed, especially when comparing the mean values of the Chemostat campaign ORFU06002 (47737 U/ml) with the mean values of RFB campaigns ORFU07001 (77653 U/ml) and ORFU07002 (93178 U/ml). (Overall, rFurin activity ranged from about 10000 to greater than 100000 U/ml; all data not shown).

The specific activity of Furin is expressed as the activity U/μg protein (see Tables 32-34). The mean specific activity for campaign ORFU06002 was 269 U/μg protein, increasing to 500 U/μg for ORFU07001 and 563 U/μg for ORFU07002, respectively. (Overall, specific activity ranged from 124-620 U/μg protein; data not shown). Thus, specific activity doubled for the two RFB campaigns, a result of the higher enzymatic activity of the RFB rFurin compared to the batches produced in Chemostat mode.

TABLE 32

Campaign ORFU06002 Capto-MMC Eluate Pool

| Furin-Lot Chemostat Mode | Furin Activity [U/ml] | Protein Content [μg/ml] | Specific rFurin Activity [U/μg] |
| --- | --- | --- | --- |
| ORFUCHR06002MMC01 | 28231 | 148 | 190.8 |
| ORFUCHR06002MMC02 | 16307 | 162 | 124.3 |
| ORFUCHR06002MMC03 | 44854 | 174 | 257.8 |
| ORFUCHR06002MMC04 | 39102 | 148 | 264.2 |
| ORFUCHR06002MMC05 | 71871 | 236 | 304.5 |
| ORFUCHR06002MMC06 | 44292 | 142 | 311.9 |
| ORFUCHR06002MMC07 | 68728 | 155 | 443.4 |
| ORFUCHR06002MMC08 | 68510 | 271 | 252.8 |
| Mean Value | 47737 | 180 | 269 |

TABLE 33

Campaign ORFU07001 Capto-MMC Eluate Pool

| Furin-Lot Repeated Fed-Batch | Furin Activity [U/ml] | Protein Content [μg/ml] | Specific rFurin Activity [U/μg] |
| --- | --- | --- | --- |
| ORFUCHR07001MMC01 | 77090 | 151 | 510.5 |
| ORFUCHR07001MMC02 | 68450 | 112 | 611.2 |
| ORFUCHR07001MMC03 | 87420 | 231 | 378.4 |
| Mean Value | 77653 | 165 | 500 |

TABLE 34

Campaign ORFU07002 Capto-MMC Eluate Pool

| Furin-Lot Repeated Fed-Batch | Furin Activity [U/ml] | Protein Content [μg/ml] | Specific rFurin Activity [U/μg] |
| --- | --- | --- | --- |
| ORFUCHR07002MMC01 | 91200 | 162 | 563.0 |
| ORFUCHR07002MMC02 | 96400 | 160 | 602.5 |
| ORFUCHR07002MMC03 | 95020 | 173 | 549.2 |
| ORFUCHR07002MMC04 | 85690 | 190 | 451.0 |
| ORFUCHR07002MMC05 | 102670 | 174 | 590.1 |
| ORFUCHR07002MMC06 | 88090 | 142 | 620.4 |
| Mean Value | 93178 | 167 | 563 |

Furin-Use-Test Activity. The Furin-Use-Test is designed to quantify the efficacy of rFurin to process pro-VWF to mature rVWF. The maturation efficacy is expressed as the amount of Furin units required for the maturation of 1 VWF Antigen unit (U Furin/U VWF). The substrate is a proVWF/VWF preparation that has been purified at Pilot scale according to the current manufacturing procedure but omitting the Furin maturation and the final purification step on Superose 6. The rVWF substrate concentration was 100 U Ag/ml (F8HL_24_01UF02-R).

Four dilutions of the sample were tested in a 1 ml Eppendorf Tube to cover specific Furin concentrations of, e.g., 0.25-2.0 U/U VWF. The reaction and dilution buffer was 100 mM HEPES, 1 mM $CaCl_2$, pH7.0 and the maturation experiment was performed for 16 hours at 37° C. under slight agitation. After the incubation the enzymatic reaction is stopped by addition of SDS-sample buffer and heating the samples for 5 minutes at >90° C. The samples are then analysed by SDS-PAGE on 8% gels using silver staining of the separated polypeptides. The specific Furin activity required to get a maturation efficacy of >95% as evaluated by visual inspection of the gels (the proVWF band should represent less than 5% compared to the mature VWF band) is then reported and used as a quality attribute of the rFurin tested.

TABLE 35

Campaign ORFU06002 Capto-MMC Eluate Pool

| Furin-Lot Chemostat Mode | Furin Activity [U/ml] | Use-test Activity [U/U] | Maturation Degree [%] |
| --- | --- | --- | --- |
| ORFUCHR06002MMC01 | 28231 | 0.7 | >95 |
| ORFUCHR06002MMC02 | 16307 | 0.4 | >95 |
| ORFUCHR06002MMC03 | 44854 | 1.1 | >95 |
| ORFUCHR06002MMC04 | 39102 | 1.3 | >95 |
| ORFUCHR06002MMC05 | 71871 | 1.0 | >95 |
| ORFUCHR06002MMC06 | 44292 | 1.0 | >95 |
| ORFUCHR06002MMC07 | 68728 | 1.0 | >95 |
| ORFUCHR06002MMC08 | 68510 | 1.0 | >95 |
| Mean Value | 47737 | 0.58 | >95 |

TABLE 36

Campaign ORFU07001 Capto-MMC Eluate Pool

| Furin-Lot Repeated Fed-Batch | Furin Activity [U/ml] | Use-test Activity [U/U] | Maturation Degree [%] |
|---|---|---|---|
| ORFUCHR07001MMC01 | 77090 | 0.5 | >95 |
| ORFUCHR07001MMC02 | 68450 | 0.5 | >95 |
| ORFUCHR07001MMC03 | 87420 | 0.5 | >95 |
| Mean Value | 77653 | 0.5 | >95 |

TABLE 37

Campaign ORFU07002 Capto-MMC Eluate Pool

| Furin-Lot Repeated Fed-Batch | Furin Activity [U/ml] | Use-test Activity [U/U] | Maturation Degree [%] |
|---|---|---|---|
| ORFUCHR07002MMC01 | 91200 | 0.5 | >95 |
| ORFUCHR07002MMC02 | 96400 | 0.5 | >95 |
| ORFUCHR07002MMC03 | 95020 | 0.5 | >95 |
| ORFUCHR07002MMC04 | 85690 | 0.3 | >95 |
| ORFUCHR07002MMC05 | 102670 | 0.6 | >95 |
| ORFUCHR07002MMC06 | 88090 | 1.0 | >95 |
| Mean Value | 93178 | 0.6 | >95 |

Good and consistent maturation activity for proVWF was found for all tested rFurin batches. The mean values of the campaigns are below 1.0 U Furin/U VWF:Ag and the maturation degree exceeds 95% in all cases. (Tables 35-37). Maturation activities of all rFurin batches are comparable and, referring to the calculated mean values of the campaigns ORFU06002, ORFU07001 and ORFU07002, almost no differences can be found between rFurin produced in Chemostat mode and RFB-mode.

Figure 12:
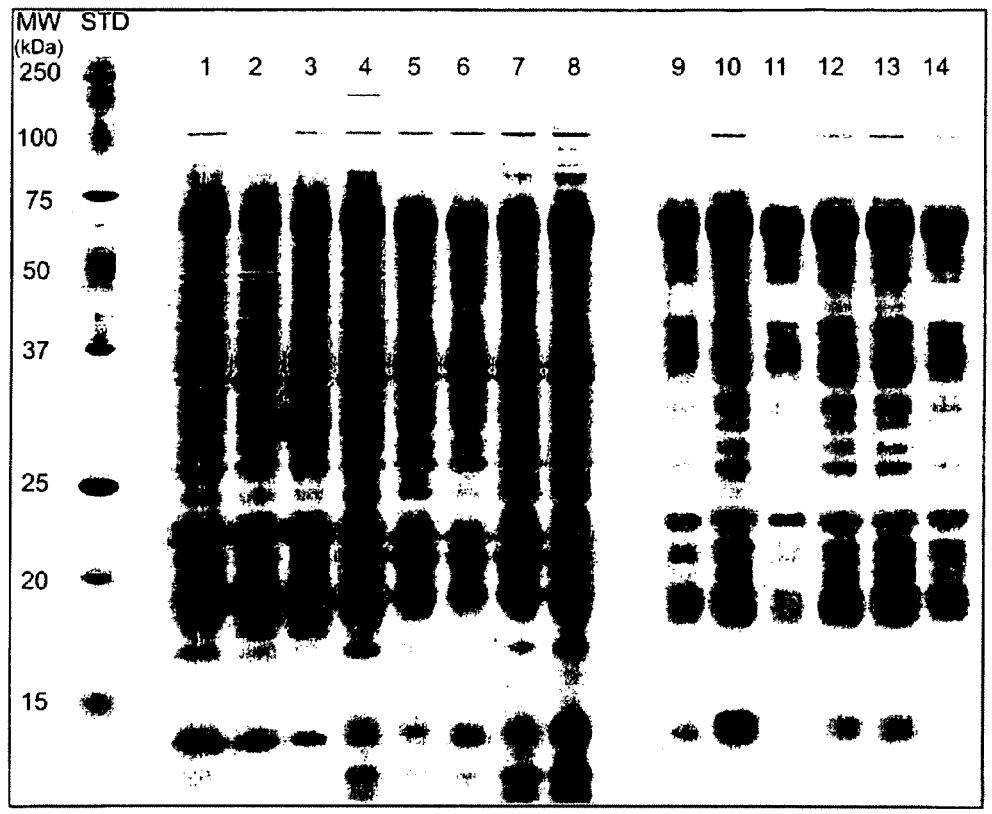
FIG. 12 shows SDS-page and silver-stain for rFurin. The band patterns of the Capto-MMC eluates of campaign ORFU06002 and ORFU07002 correlate to a high degree; all samples show a prominent Furin band at approx. 60 kDa. A trend to slightly lower molecular weight of the Furin bands is visible in samples of campaign ORFU06002 from batches MMC01 to MMC08 (FIG. 12, lanes 1-8).

Furin SDS-PAGE and Silver Stain. 8% SDS-PAGE with silver staining and Western blot analysis was performed for all rFurin batches to ensure consistent quality and visualize the degree of impurity. As seen in FIG. 12, the band patterns of the Capto-MMC eluates of campaign ORFU06002 and ORFU07002 correlate to a high degree; all samples show a prominent Furin band at approx. 60 kDa. A trend to slightly lower molecular weight of the Furin bands is visible in samples of campaign ORFU06002 from batches MMC01 to MMC08 (FIG. 12, lanes 1-8). Samples of those batches were deglycosylated with the effect that this trend was not visible anymore in subsequent SDS-PAGE with silvers staining (data not shown), supporting the assumption that during campaign ORFU06002, rFurin was glycosylated slightly different or to a lesser degree in course of ongoing fermentation. This trend was not noticed in RFB campaign ORFU07002, suggesting constant glycosylation of the rFurin during the whole campaign. The impurities in batches from ORFU06002 and ORFU07002 are almost completely the same; however, samples from the RFB-mode campaign ORFU07002 show less intense bands in the 40 kDa region, polypeptides that were particularly strong enriched in samples of campaign ORFU06002.

Figure 13:
FIG. 13 shows the Western blot analysis of samples using a monoclonal anti-Furin antibody.

SDS-PAGE Western Blot. Western blot analysis for all samples was performed using a monoclonal anti-Furin antibody (FIG. 13). The prominent band at ~60 kDa can be identified as the Furin band and is found in all samples. Comparability of the samples is very high. Slight variations in band intensity are due to the different Furin concentration in the samples. Overall, SDS-PAGE analysis underlines the comparability of rFurin produced in Chemostat and RFB mode.

Figure 14:
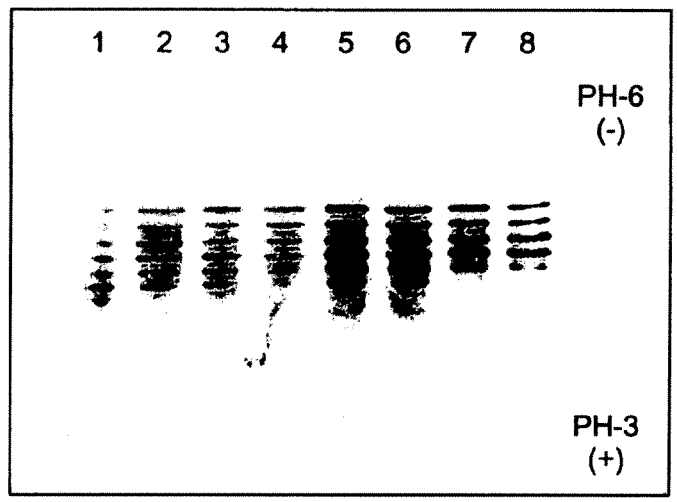
FIG. 14 shows the specific band patterns for rFurin from isoelectric focusing (IEF) and subsequent Western blotting of rFurin samples of campaign ORFU06002.

To support conventional SDS-PAGE, Isoelectric Focusing (IEF) was performed on samples of campaigns ORFU06002 and ORFU07002. IEF was performed between pH 7.0 and pH 3.0, using vertical IEF. The polypeptides were visualized with Coomassie staining and Western blot analysis. IEF and subsequent Western blotting of rFurin samples of campaign ORFU06002 provided specific band patterns for Furin (see FIG. 14). Up to seven separate bands in the region of pH 4.5 to pH 5.5 can be identified, with at least five bands present in all samples.

Figure 15:
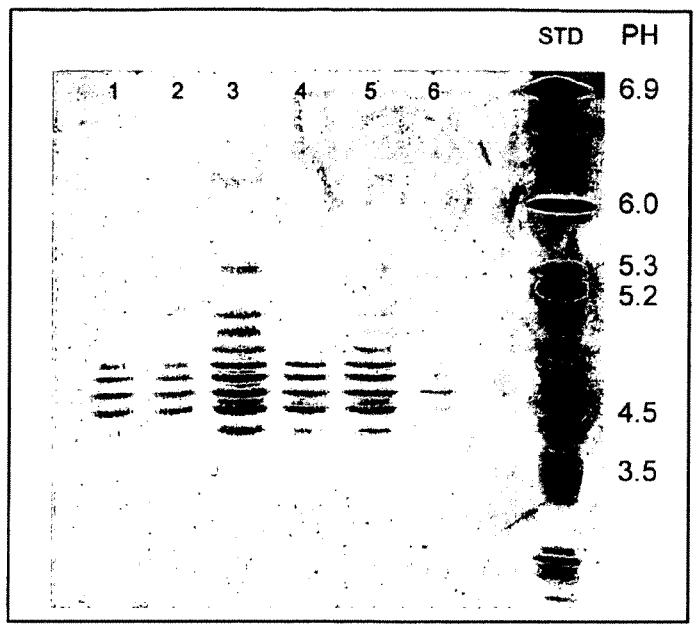
FIG. 15 shows the specific band patterns for rFurin from isoelectric focusing (IEF) and subsequent Western blotting of rFurin samples of campaign ORFU07002.

IEF of samples of campaign ORFU07002 was carried out using Coomassie staining and Western blot analysis for visualization. Coomassie staining reveals the specific band pattern with all samples showing at minimum five separate bands in the range of pH 4.5 to pH 5.5, and up to eight bands can be identified (see FIG. 15, Lane 3).

Figure 16:
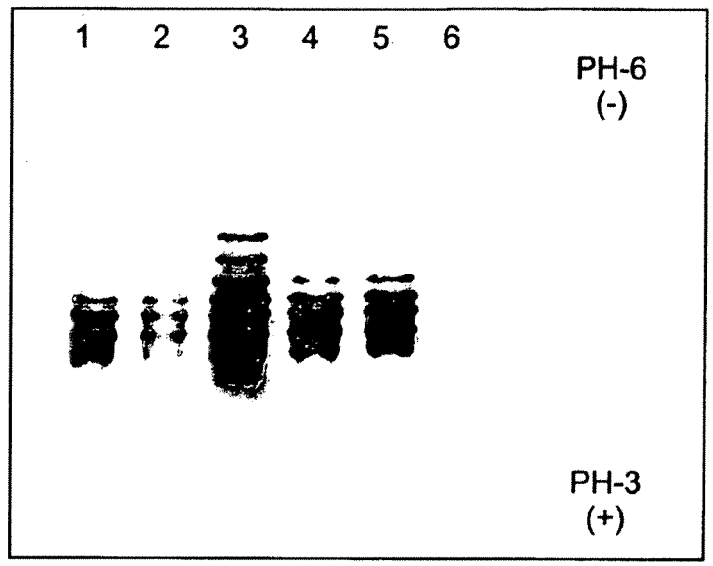
FIG. 16 shows Western blot results for rFurin from isoelectric focusing (IEF) and subsequent Western blotting of rFurin samples of campaign ORFU07002.
Figure 17:
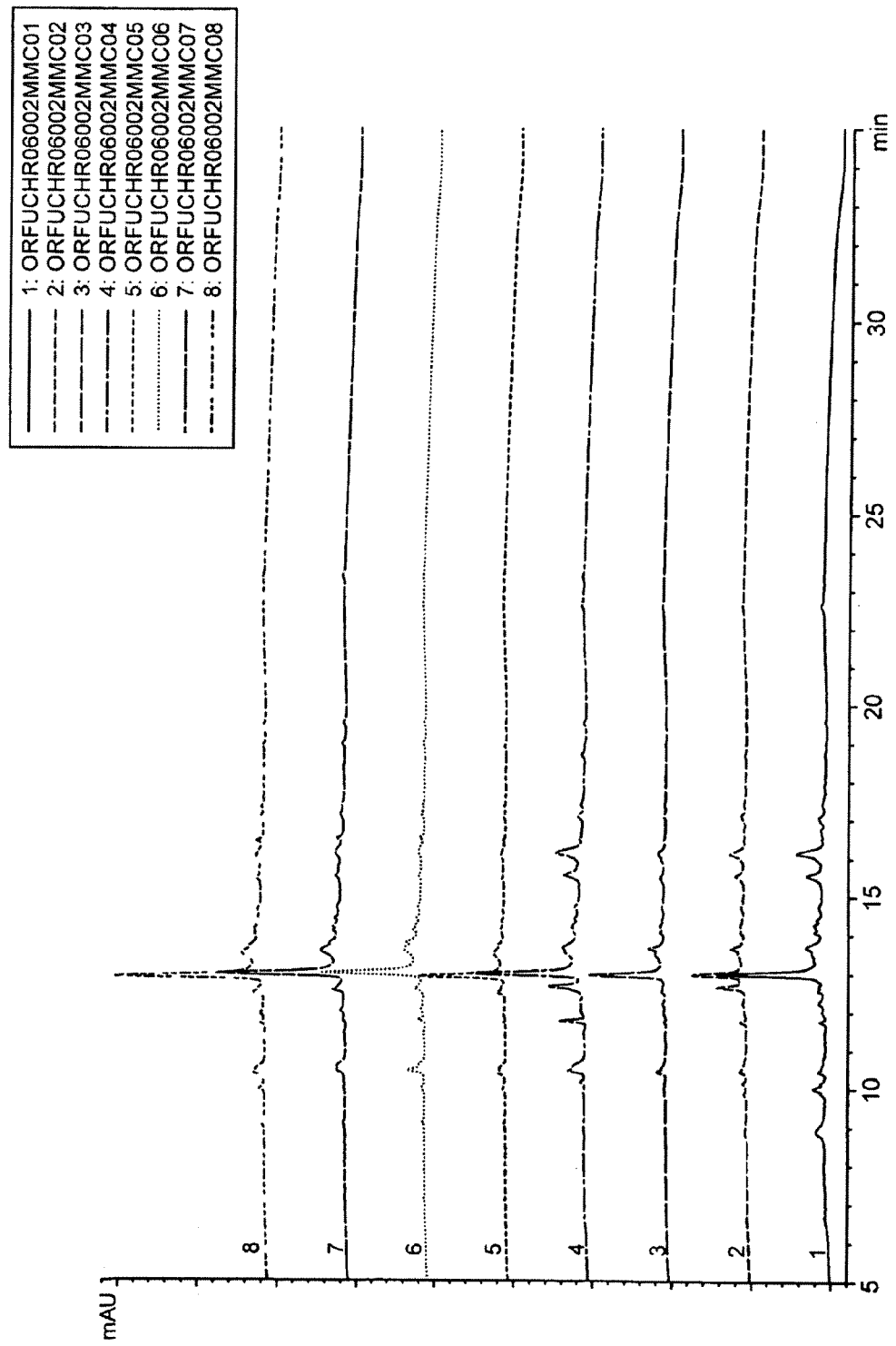
FIG. 17 shows Furin Reverse Phase HPLC for samples from campaign ORFU06002 (Capto-MMC eluates). Samples were tested with C4 RP-HPLC in order to establish a fingerprint pattern for rFurin.

Western blot analysis (see FIG. 16) corroborates these results, with some samples showing not all the bands visible in the Coomassie gel (see FIG. 17), probably due to incomplete transfer of the proteins from the gel to the blotting membrane.

Figure 18:
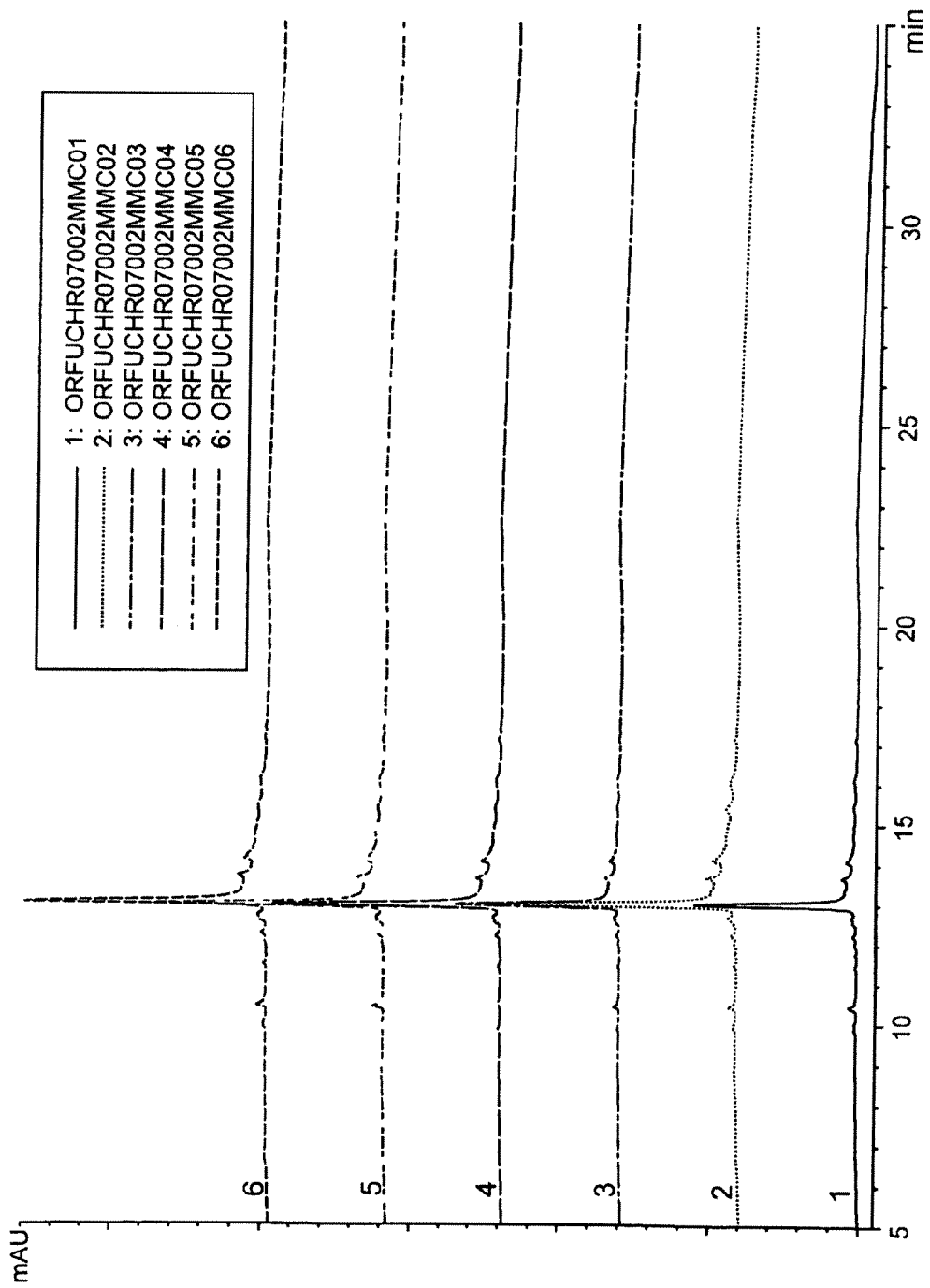
FIG. 18 shows Furin Reverse Phase HPLC for samples from campaign ORFU07002 (Capto-MMC eluates). Samples were tested with C4 RP-HPLC in order to establish a fingerprint pattern for rFurin.

Furin Reverse Phase HPLC. Samples from campaigns ORFU06002 and ORFU07003 (Capto-MMC eluates) were tested with C4 RP-HPLC in order to establish a fingerprint pattern for rFurin. The peak patterns of the samples of the two campaigns were compared (see FIG. 17 and FIG. 18).

Chromatograms of all tested samples show a characteristic main peak at a retention time of approx. 13 min., which can be assigned to Furin. The peak heights correlate well with the Furin concentration in the samples. Other protein impurities can be seen as minor peaks in the range of 8 min to 17 min. All samples from campaign ORFU07002 show significantly less and smaller peaks from impurities than those from ORFU06002. This fact is well in accordance with the results of SDS-PAGE, as in the RFB mode campaign ORFU07002 a smaller number and decreased amount of impurities were found.

Analytical data obtained from the above discussed characterization methods prove very good comparability of the rFurin produced in both Chemostat mode and RFB mode. No major differences in rFurin quality could be detected from the data available, however rFurin batches produced in RFB mode showed higher specific activity and less impurities compared to production in Chemostat mode. The chromatographic step accounts for the very low Host Cell Protein and Host Cell DNA content in the Bulk Drug Substance (BDS). At least a complete production process consisting of a RFB-fermentation and the whole down-stream processing (Filtration, UF/DF, Capto-MMC chromatography) is maybe easier to be implemented for the commercial production of rFurin, e.g. in Single Use Bioreactor (SUB) systems.

Example 6

Safety, Sterility, and Stability Testing

This example describes the safety, sterility, and stability testing that is performed to determine and maintain the quality of the CHO cell bank. Testing on sterility/mycoplasma has to be performed in accordance to requests of the ICH-Guideline Q5D. The quality of the cell bank has to be checked by determination of average viability and cell density of the thawed cells and subsequent growth rate of the cultures.

Cells were tested for viral safety (Table 38), genetic stability (Table 39), and identity (Table 40). Cells were found to be sterile, free of mycoplasma, free from extraneous agents, free from retroviruses, negative for MVM virus, negative for adventitious viruses, negative for rodent viruses, free from porcine and bovine viruses, and free from Cache Varney virus (CVV).

Cell banks were examined with regard to the Furin producer/non-producer ratio by FACS analysis. They are also tested for their long term stability (ability to produce Furin over a period of time). Further, the secreted Furin produced under serum-free conditions has to be investigated with respect to generated isoforms. All data should indicate that stable growth and Furin production can be achieved using these cell banks.

Cells from the MCB/WCB should show stable growth and Furin expression over the entire production process.

TABLE 38

| Viral Safety Program | | | |
|---|---|---|---|
| Test | MCB | WCN | MEPC |
| Adventitious viruses in vitro (CHO, A9, Vero, MRC-5 Cells) | x | x | x |
| Adventitious viruses in vivo (in suckling mice, adult mice, guinea pigs, and embryonated eggs) | x | (x) | x |
| Rodent viruses MAP test with LCMV challenge | x | — | — |
| Rodent viruses HAP | x | — | — |
| Rodent viruses MMV (in vitro assay) | x | — | x |
| Retroviruses EM (Transmission electron microscopic examination) | x | — | x |
| Retroviruses Retroviral Infectitvity Assay with Pert Endpoint | x | — | x |
| Retroviruses Ex S + L- (in vitro detection of xenotropic retroviruses by Mink S + L-Focus) | x | — | x |
| Retroviruses/Co cultivation Detection of infectious retroviruses by co-cultivation with HEK 293 cells (5 passages) | — | — | x |
| Bovine virus: Detection of viral contaminants in Bovine serum according CMPC & US 9CFR requirements | x | — | — |
| Porcine virus: In vitro assay, detection of porcine viral contaminants using PPK indicator cells according to 9 CFR | x | — | — |
| PCR Bovine polyomavirus | x | — | x |
| Real time PCR of Cache Valley Virus (CVV) | x | — | x |

(x) viral testing has not to be performed on the WCB from which the MEPC have been prepared

TABLE 39

| Genetic Stability Program | | | |
|---|---|---|---|
| Test | MCB | WCB | MEPC |
| Productivity: Furin activity assay | x | x | x |
| Sequencing | x | — | x |
| quantitative PCR (gene copy number) | x | — | x |

TABLE 39-continued

| Genetic Stability Program | | | |
|---|---|---|---|
| Test | MCB | WCB | MEPC |
| Southern Blot | x | — | x |
| Northern Blot | x | — | x |

TABLE 40

| Identity Program | | | |
|---|---|---|---|
| Test | MCB | WCB | MEPC |
| Isoenzyme analysis | x | x | x |

The present invention has been described in terms of particular embodiments found or proposed to comprise preferred modes for the practice of then invention. It will be appreciated by those of ordinary skill in the art that, in light of the present disclosure, numerous modifications and changes can be made in the particular embodiments exemplified without departing from the intended scope of the invention. Therefore, it is intended that the appended claims cover all such equivalent variations which come within the scope of the invention as claimed.

What is claimed is:

1. A composition comprising substantially animal protein-free recombinant furin lacking transmembrane and cytoplasmic domains comprising a specific activity of at least or about 400 U/μg protein and host cell protein at a concentration less than about 1.0 ng protein/U furin activity, or host cell DNA at a concentration less than about 0.5 pg DNA/U furin activity, and essentially lacking contaminating proteins from serum.

2. The composition of claim 1 comprising recombinant furin at an activity of at least or about 10000 U furin/ml.

3. The composition of claim 1 comprising recombinant furin at an activity of at least or about 450 U/μg.

4. A method of making the composition of claim 1 comprising growing a host cell transformed or transfected with a polynucleotide encoding secreted recombinant furin lacking transmembrane and cytoplasmic domains in serum-free medium in a repeated fed batch process under conditions that permit secretion of the furin into the medium, binding the secreted furin on a multimodal cation exchange resin to remove host cell protein, host cell DNA, or a combination thereof; and recovering the secreted recombinant furin from the multimodal cation exchange resin.

5. The method of claim 4 comprising the step of adapting the host cell to grow in medium with increasingly lower concentrations of serum until all serum is removed from the medium.

6. The method of claim 4 comprising transferring the host cell from growth in medium comprising serum to growth in serum-free medium.

7. The method of claim 5 or 6, wherein the host cell is a Chinese Hamster Ovary (CHO) cell.

8. A method of processing a pro-protein comprising a furin cleavage site comprising the step of contacting the pro-protein comprising the furin cleavage site with the composition of claim 1 under conditions to cleave a pro-peptide from the pro-protein to form a mature protein.

9. The method of claim 8, wherein the mature protein is von Willebrand Factor.

10. The method of claim 8, wherein the mature protein is Factor VIII.

11. The composition of claim 1, wherein the host cell is a Chinese Hamster Ovary (CHO) cell.

12. The composition of claim 1 comprising recombinant furin at an activity of at least or about 500 U/μg.

* * * * *